(12) United States Patent
Lee et al.

(10) Patent No.: US 6,505,067 B1
(45) Date of Patent: Jan. 7, 2003

(54) SYSTEM AND METHOD FOR DERIVING A VIRTUAL ECG OR EGM SIGNAL

(75) Inventors: Brian B. Lee, Golden Valley, MN (US); Eric J. Panken, Edina, MN (US); James D. Reinke, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/721,275

(22) Filed: Nov. 22, 2000

(51) Int. Cl.$^7$ .............................................. A61B 5/0402
(52) U.S. Cl. ...................................................... 600/509
(58) Field of Search ................................ 600/509, 523, 600/512

(56) References Cited

U.S. PATENT DOCUMENTS

| | | |
|---|---|---|
| 3,548,813 A | 12/1970 | Berner |
| 3,983,867 A | 10/1976 | Case ..................... 128/2.06 G |
| 4,023,565 A | 5/1977 | Ohlsson .................. 128/206 B |
| 4,082,086 A | 4/1978 | Page et al. .............. 128/2.06 E |
| 4,136,690 A | 1/1979 | Anderson et al. |
| 4,170,227 A | 10/1979 | Feldman et al. ............. 128/704 |
| 4,263,919 A | 4/1981 | Levin .......................... 128/708 |
| 4,476,868 A | 10/1984 | Thompson ............ 128/419 PG |
| 4,569,357 A | 2/1986 | Sanz et al. |
| 4,593,702 A | 6/1986 | Kepski et al. ............... 128/696 |
| 4,850,370 A | 7/1989 | Dower ........................ 128/699 |
| 5,052,388 A | 10/1991 | Sivula et al. ......... 128/419 PG |
| 5,231,990 A | 8/1993 | Gauglitz ..................... 128/697 |
| 5,331,966 A | 7/1994 | Bennett et al. ............. 128/696 |
| 5,345,362 A | 9/1994 | Winkler ...................... 361/681 |
| 5,366,687 A | 11/1994 | Dalzell, Jr. et al. ........... 419/35 |
| 5,711,304 A | 1/1998 | Dower ........................ 128/696 |
| 6,038,469 A | 3/2000 | Karlsson et al. ............ 600/512 |

FOREIGN PATENT DOCUMENTS

| | | |
|---|---|---|
| DE | 197 49 768 A | 5/1999 |
| EP | 1 010 968 A | 6/2000 |

Primary Examiner—Scott M. Getzow
(74) Attorney, Agent, or Firm—GirmaWolde-Michael; Michael C. Soldner

(57) ABSTRACT

A system and method for obtaining a virtual physiologic voltage signal between a first predetermined point in a second selected point in the body is disclosed. At least three electrodes are used to measure two voltage signals S1 and S2 in a body. In one embodiment, the signal S1 is measured between a first electrode and a common electrode, and the signal S2 is measured between a second electrode and the common electrode. A selected point within the body may be chosen to define a pair of virtual electrodes existing between this selected point and the common electrode. An approximation of the voltage signal S as could be measured between electrodes positioned at these virtual electrode locations may be derived as a function of S1, S2, and θ, wherein θ is the angle between the directional vector U1 for the signal S1 and the directional vector U for the signal S. According to the inventive system and method, the signal value for S is also dependent on the distances between the electrode pairs, on the angle β between directional vectors U1 and U2, and on the distance between the virtual electrodes. The current invention may be utilized with electrodes that are positioned either externally on the surface of, or implanted within, a body. According to one aspect of the invention, a user may employ a user interface to select the values of θ, β, and the electrode spacings. Alternatively, ones of these parameters may be predetermined by the system. In another embodiment, the system could derive the signal S over a predetermined range of values for the angle θ. The system may then select the angle of θ resulting in the derived signal S that exhibits a desired waveform morphology.

35 Claims, 20 Drawing Sheets

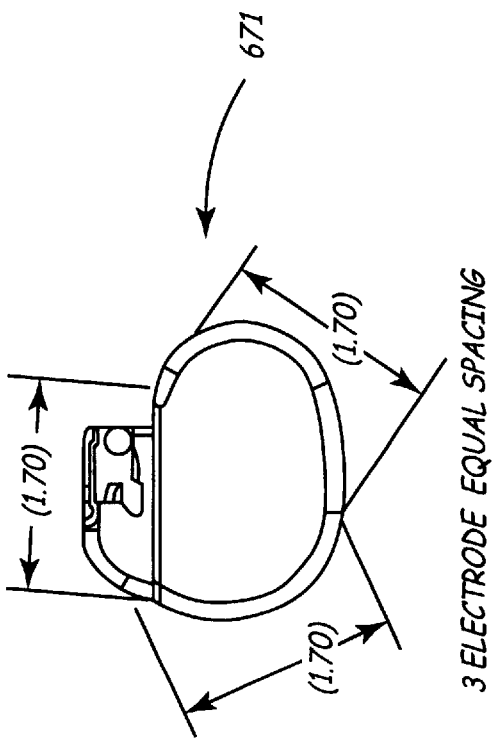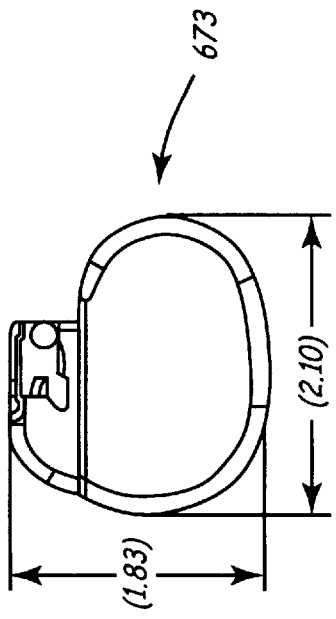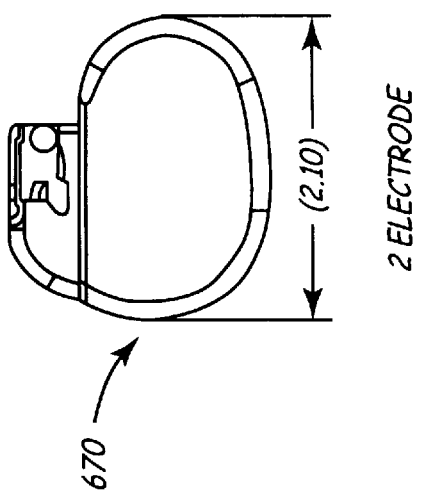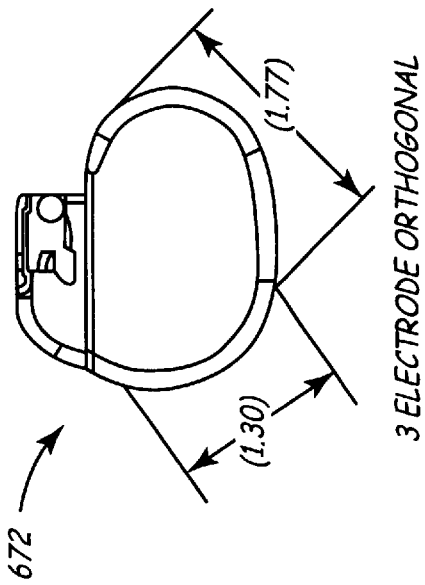
FIG. 10

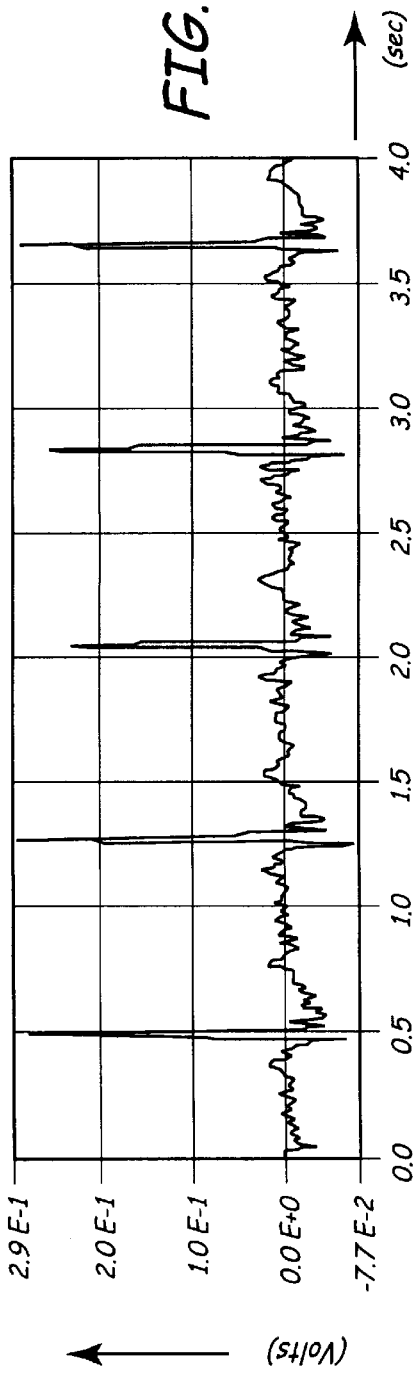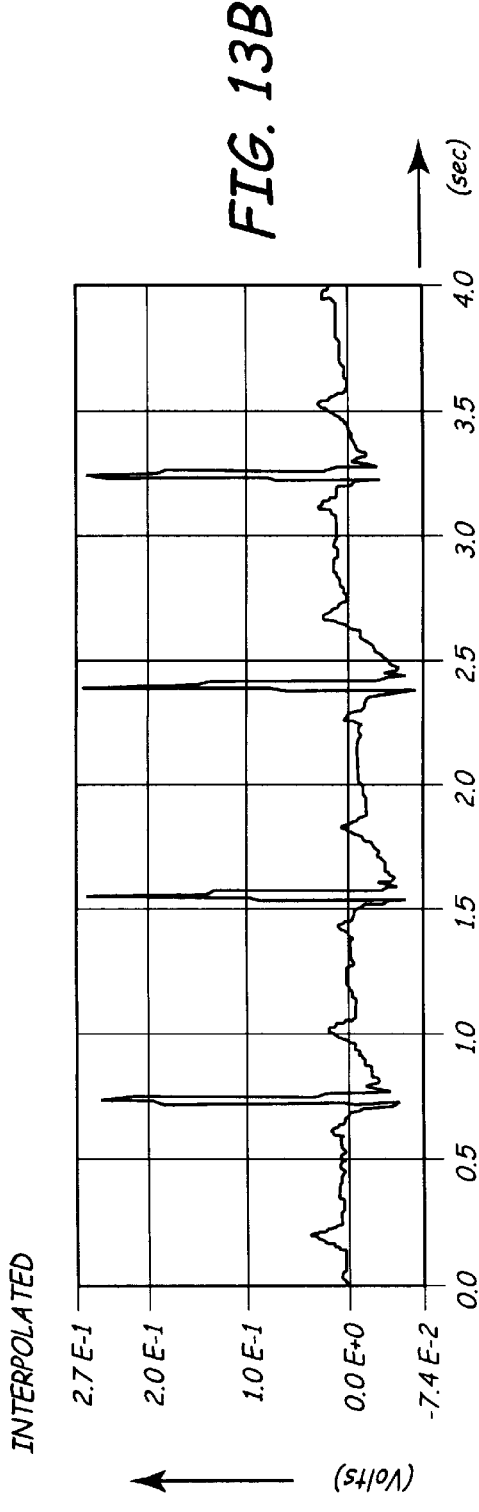

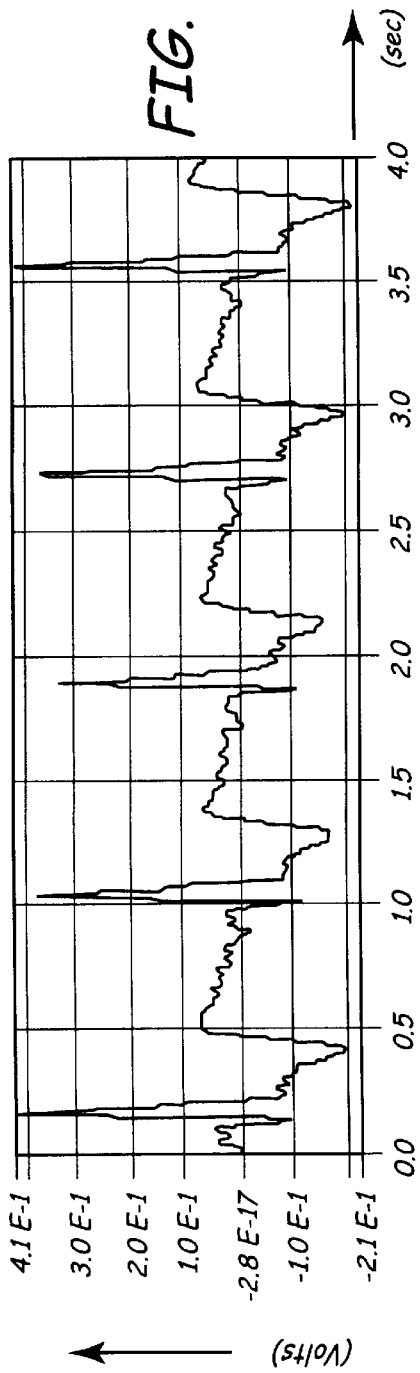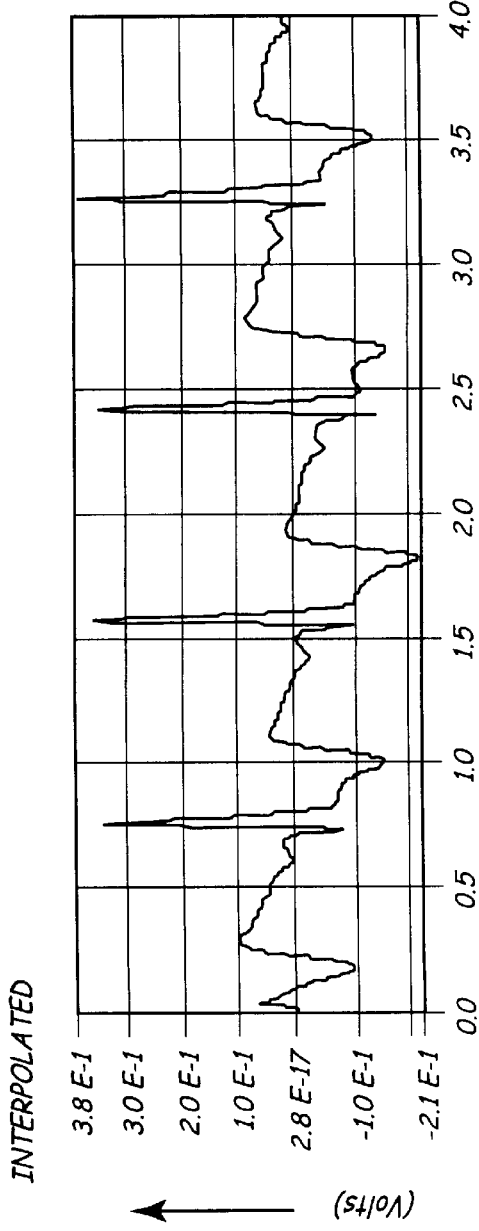

SYSTEM AND METHOD FOR DERIVING A VIRTUAL ECG OR EGM SIGNAL

CROSS-REFERENCE TO CO-PENDING APPLICATIONS

This application is related to U.S. Application Ser. No. 09/718,689 entitled "System and Method for Non-Invasive Determination of Optimal Orientation of an Implantable Sensing Device" to Lee et al. filed on even date herewith, and which is incorporated by reference in its entirety.

FIELD OF THE INVENTION

This invention relates to electrophysiology; and, more particularly, to a system and method for utilizing two or more physiologic voltage potential signals to determine the voltage potential that would be measured between a virtual electrode pair placed at a predetermined location on, or within, a body.

BACKGROUND OF THE INVENTION

At any given point in time, a selected point within a living body may be at a different voltage potential than that of another selected point in the body. Moreover, the voltage potential at a given point is likely changing with time. Electrodes positioned at two distinct points will therefore measure a potential difference signal between those two points that is varying over time.

A common example of a system of measuring potential differences within the human body is provided by the electrocardiogram (ECG), which refers to a plot against time of the varying potential differences existing between various standard electrode pairs positioned on the surface of the body. A conventional ECG measurement will include twelve signal measurements, also referred to as "leads", that are taken using a set of standard electrodes pairs.

FIG. 1 illustrates the ten standard electrode positions used to obtain a twelve-lead ECG measurement. Electrodes RA, LA, and LL are positioned on a patient's right arm, left arm, and left leg respectively, and a ground is generally placed on the right leg (RL). Other electrodes V1 through V6 are placed on the patient's chest. Various electrode pairs are used to obtain the standard set of twelve leads included in an ECG measurement.

Three of the signals measured are commonly referred to as Lead I, Lead II, and Lead III. These refer to measurements between RA and LA, between RA and LL, and between LA and LL, respectively. These three signal measurements comprise what is called Einthoven's triangle, shown in FIG. 2. This triangle is commonly used to show the relationship between the measured electrical signals and the lead positions. This can be expressed in equation form as follows:

$$\text{lead } II = \text{lead} I + \text{lead} III.$$

This concept is based on Kirchoff's voltage law, wherein the voltage signals as measured between the right to left arm, between left arm to left leg, and between left leg to right arm may be added to obtain a sum of zero if the first point in each pair is considered the voltage reference point. As is evident from the foregoing equation, any one of the signals of Einthoven's triangle may be approximated if the other two signals are known. By extending this concept, all of the signals included in the standard 12-lead ECG may be approximated if only two of the signals are known.

Systems have been developed to utilize ones of the 12-signal ECG measurements to derive other measurements. For example, U.S. Pat. No. 5,231,990 to Gauglitz describes a circuit that adds various ones of the standard ECG signals to generate other ones of the standard ECG signals. A similar system is described in U.S. Pat. No. 5,711,304 to Dower which discloses using ones of the 12-lead ECG signals to calculate the signals that exist at predetermined non-standard ECG positions on a body. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems that combine surface ECG signals for artifact rejection.

U.S. Pat. No. 6,038,469 to Karlsson et al. discloses a cardiac monitoring system that continuously stores three perpendicular leads X, Y, and Z, and derives a standard 12-signal ECG signal there from in real time. Another similar system is described in U.S. Pat. No. 4,850,370 to Dower, which discloses the use of four electrode positions on the chest of a patient to derive xyz vector cardiographic signals or the standard 12-lead ECG signal set. U.S. Pat. No. 5,366,687 to Evan et al. discloses the use of a standard 10-electrode ECG configuration to derive a spatial distribution of signals representative that would be collected from a system having 192 electrodes.

Numerous body surface ECG monitoring electrode systems have been employed in the past in detecting the ECG and conducting vector cardiographic studies. For example, U.S. Pat. No. 4,082,086 issued to Page, et al., discloses a four electrode orthogonal array that may be applied to the patient's skin both for convenience and to ensure the precise orientation of one electrode to the other. U.S. Pat. No. 3,983,867 issued to Case describes a vector cardiography system employing ECG electrodes disposed on the patient in normal locations and a hex axial reference system orthogonal display for displaying ECG signals of voltage versus time generated across sampled bipolar electrode pairs.

The above-described systems utilize standard ECG measurements to derive other standard measurements. Similar techniques may be performed using Subcutaneous Electrode Arrays (SEAs) located under a patient's skin. U.S. Pat. No. 5,331,966 issued to Bennett, incorporated herein by reference, discloses a method and apparatus for providing an enhanced capability of detecting and gathering electrical cardiac signals via an array of relatively closely spaced subcutaneous electrodes located on the surface of an implanted device. More recently, U.S. patent application Ser. No. 09/697,438 filed Oct. 26, 2000 entitled "Surround Shroud Connector and Electrode Housings for a Subcutaneous Electrode Array and Leadless ECGs", by Ceballos, et al., incorporated herein by reference in its totality, discloses an alternate method and apparatus for detecting electrical cardiac signals via an array of subcutaneous electrodes located on a shroud circumferentially placed on the perimeter of an implanted pacemaker. An associated U.S. patent application Ser. No. 09/703,152 filed Oct. 31, 2000 entitled "Subcutaneous Electrode for Sensing Electrical Signals of the Heart" by Brabec et al., incorporated herein by reference in its totality, discloses the use of a spiral electrode using in conjunction with the shroud described in the '438 application. In addition, U.S. patent application Ser. No. 09/696,365 filed Oct. 25, 2000 entitled "Multilayer Ceramic Electrodes for Sensing Cardiac Depolarization Signals", by Guck et al, disclosed the use of multi-layer ceramic electrodes placed into recesses incorporated along and into the peripheral edge of the implantable pacemaker.

As discussed above, both ECG leads and SEA arrays may be used to derive standard measurements. However, standard measurements may not always provide the desired diagnostic information. In some situations, non-standard signals provide more relevant information than is provided by a standard set of signals. For example, in situations in which the optimal angle of placement for an implantable device is to be determined, it is desirable to calculate voltage differences at all possible angles of implant using an electrode spacing that approximates the spacing of electrode pairs as they will exist after implant. What is needed, therefore, is a system and method that extends the prior art concepts to provide a system that utilizes non-standard measurements including measurements derived from implanted electrodes, to automatically generate an infinite number of other non-standard measurements.

BRIEF DESCRIPTION OF THE DRAWINGS

FIG. 10 is an illustration of the various possible electrode sites that may be located along the perimeter of the implanted pacemaker within the compliant shroud when a subcutaneous electrode array is used to practice the current invention.

FIG. 13A is a graph of a measurement physiological signal with respect to time wherein the signal is measured using an electrode pair positioned to have an angle θ of 15 degrees with respect to a first measured signal.

FIG. 13B illustrates the comparable virtual signal S derived to approximate the signal shown measured in FIG. 13A.

FIG. 14A through FIG. 20B are graphs comparing measured physiologic signal values to respective interpolated values for various values of angle θ.

SUMMARY OF THE INVENTION

Figure 1:
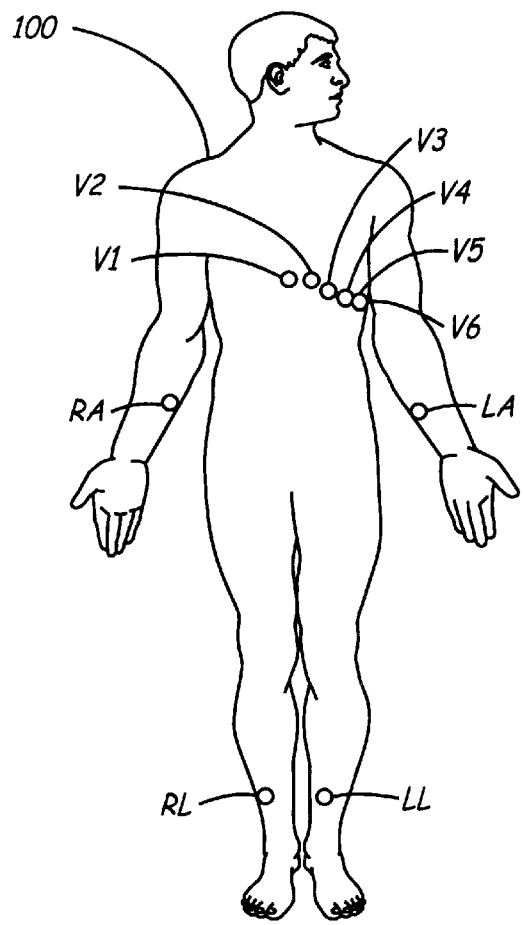
FIG. 1 is a diagram illustrating the ten standard electrode positions used to obtain a twelve-lead ECG measurement.
Figure 2:
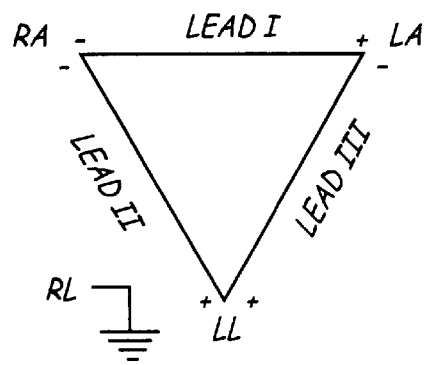
FIG. 2 is a block diagram illustrating the three signal measurements included in Einthoven's triangle.

The present invention provides a system and method for obtaining a virtual physiologic voltage signal between a first predetermined point and any other selectable point. This virtual signal is an approximation of an actual signal that would be measured between the two points.

The current invention utilizes at least three electrodes to measure two voltage signals S1 and S2. In one embodiment, the signal S1 is measured between a first electrode and a common electrode, and the signal S2 is measured between a second electrode and the common electrode. Signal S1 may be described as having a directional vector U1, and signal S2 may be defined as having a directional vector U2.

Next, another point is selected to define a pair of virtual electrodes existing between this selected point and the common electrode. An approximation of the signal S as would be measured between this virtual electrode pair may be derived as a function of S1, S2, and θ, wherein θ is the angle between the directional vector U1 and the directional vector U for the signal S. According to the inventive system and method, the signal value for S is also dependent on the distances between the electrode pairs, on the angle β between directional vectors U1 and U2, and on the distance between the virtual electrode. Applicants' studies have indicated that the derivation for signal S provided by the current invention closely approximates the signal that would actually be measured between the virtual electrode pair.

In another embodiment of the invention, four electrodes may be employed to obtain the measurements S1 and S2, with a respective pair of the four electrodes being used to obtain each of the measurements. In this embodiment, the electrodes are positioned such that the linear segment defined between a first electrode pair intersects with the linear segment defined between a second electrode pair at a point that may be referred to as the virtual common electrode. In a manner similar to that discussed above, the signal S between this virtual common electrode and any other point may be derived as a function of β, θ, S1, S2, and the distances between the various electrodes. This signal S closely approximates the signal that could be measured between the virtual electrode pair.

In one embodiment of the invention, the time-varying signal value S may be generated and displayed in real-time as the measurements for S1 and S2 are obtained. In another embodiment, the signal S may be derived using previously-stored signal values for S1 and S2.

The current invention may be utilized with electrodes that are positioned either externally on the surface of, or implanted within, a body. For internally-placed electrodes, the electrodes may be positioned on the external housing of an IMD. For externally-positioned electrodes, the electrodes may be carried on an electrode patch, or carried on leads of the type typically used to obtain ECG measurements.

According to one aspect of the invention, a user interface may be utilized to enter the values of θ, β, and the distances between the electrodes. In another embodiment, values for β and the distances between electrodes may be fixed. In yet another embodiment, one or more of these parameter values may be readable as from jumper or switch settings positioned on a device carrying the electrodes. For example, an electrode patch may include either user-selectable or hard-coded jumpers that may be readable by a processor for determining the various parameter values needed to practice the current inventive method.

The current inventive system may be implemented using a processing circuit to derive the value for S. This processing circuit may function entirely under software control to perform the steps needed to determine the signal value S. Alternatively, some or all of the steps performed to obtain the approximated signal value S may be completed under hardware control as may be accomplished, for example, using an arithmetic co-processor circuit. Moreover, when implanted electrodes are used to obtain the signal values S1 and S2, a first portion of the processing circuit may be included within an IMD, and second portion of the processing circuit may be located in a monitoring device that is external to the implantable medical device. Some or all of the steps required to perform the inventive method may be implemented within the internal processing circuit. Partially or fully-processed signal data may then be transferred via a communication circuit such as a telemetry device to the external device for additional processing, if desired. Alternatively, the external device may perform all signal processing.

Some, or all, of the steps associated with the inventive method may be completed in real time as the values for S1 and S2 are measured. Alternatively, the processing may be performed on previously-stored waveform measurements for S1 and S2. Thus, the storing of the values S1 and S2 is sufficient to retain all information necessary to allow a user to later reconstruct a signal having any other directional vector. This provides both flexibility, reduces the amount of memory required to store measured signal values, and may further reduce processing requirements.

In one embodiment, the user selects the value for $\theta$ using some type of user interface mechanism such as a dial, knob, or switch setting. For example, rotation of a dial or knob in a predetermined direction and at a predetermined deflection angle could be employed to indicate $\theta$. Moreover, $\theta$ could be selectable in any defined increment value. For instance, $\theta$ could be selectable in relatively small increments such as 0.1 degrees, or in larger increments such as 15 degrees.

In another embodiment, the system could derive the signal S for a predetermined range of values for the angle $\theta$. The system may then select the angle of $\theta$ resulting in the signal S that best satisfies some user-specified waveform criterion. For example, the system may select, based on user-specified criterion, the angle $\theta$ that results in an ECG signal S that has the largest positive-going QRS complex. The range and incremental variation to be used for $\theta$ could also be user-specified.

The current inventive system and method provides many advantages over conventional systems. Only three electrodes are needed to derive a signal having any selectable directional vector. This both reduces the amount of hardware needed to acquire the desired signal values, and/or eliminates the need to re-position electrodes. This saves time, and also reduces system costs. Additionally, the reduction in the number of electrodes placed on a given surface can minimize the disruption in the potential fields that are being measured, providing better signal reception.

DETAILED DESCRIPTION OF THE PREFERRED EMBODIMENT

The current invention provides a system and method for measuring voltage signals within a patient's body using at least three electrodes positioned either external to, or internal to the patient. For example, these electrodes may be positioned either on an external body surface, or alternatively, may be positioned under the skin. Externally-positioned electrodes are commonly utilized, for example, to measure the ECG signals of the heart using an external monitoring device such as an ECG monitor or a Holter monitor. The latter approach may be accomplished using a Subcutaneous Electrode Array (SEA) of the type included on the housing of an Implantable Medical Device (IMD). Such a device is described and discussed in commonly assigned U.S. Pat. No. 5,331,966, incorporated by reference in it entirety.

Figure 3:
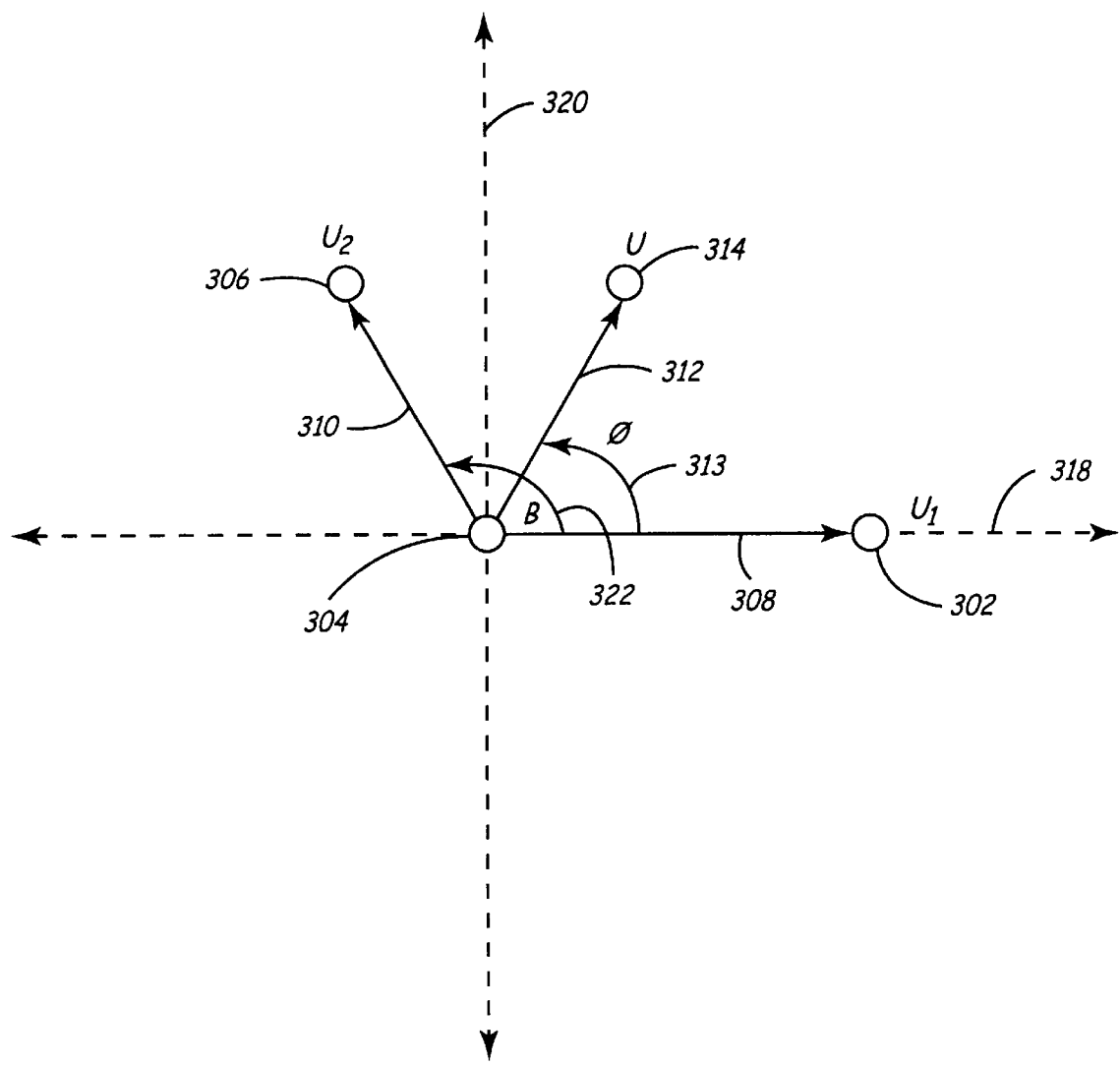
FIG. 3 is a vector diagram representing three electrodes that may be positioned in any orientation with respect to each other.

FIG. 3 is a vector diagram representing three electrodes 302, 304, and 306 that may be positioned in any orientation with respect to each other. For discussion purposes, it will be assumed the three electrodes are placed on a patient's chest to measure ECG signals, but it will be understood these electrodes could be placed anywhere on, or implanted within, a patient's body. Preferably, the electrodes that are implanted within a patient's body will reside on an external surface of an IMD. However, electrodes carried on relatively closely-spaced leads may also be used to obtain signal measurements. For example, electrodes carried on two closely-spaced distal ends of a single bifurcated lead may be used to obtain the signal measurements contemplated by the current invention.

Using the three electrodes of FIG. 3, a first voltage potential S1 308 may be measured between electrode 302 and common electrode 304. A second voltage potential S2 310 may be measured between electrode 306 and common electrode 304. Using these measurements, an automated method may be employed to determine a virtual signal S 312. The signal S may have any arbitrary directional vector located within the plane defined by electrodes 302, 304, and 306. The orientation of this vector may be described using the angle $\theta$ 313. Studies have shown that this virtual signal S 312 as derived using actual signals S1 and S2 closely approximates the signal that would be measured between an electrode at position 314 that is a user-selectable distance D from the common electrode 304. This is discussed in detail below.

The method used to determine the virtual signal S is based on vector arithmetic principles. To illustrate, an X axis 318 and Y axis 320 (both shown dashed) may be super-imposed on FIG. 3, with the common electrode being positioned as the intersection of the X and Y axis. The X axis is shown coinciding with the direction of signal S1, although this is an arbitrary selection designed to simplify the following discussion. The signal S1 may now be described as having a directional vector U1 having coordinates of (1,0). Similarly, signal S2 may be described as having a directional vector U2 with coordinates of (cos $\beta$, sin $\beta$), wherein $\beta$ 322 is the angle measured counter-clockwise between U1 and signal S2. Finally, the directional vector U of signal S may be described as having the coordinates (cos $\theta$, sin $\theta$), wherein $\theta$ is the angle measured counter-clockwise between U1 and signal S.

According to the principles of vector arithmetic, the directional vector U may be defined as a function of the two directional vectors U1 and U2 as follows:

$$U=(A \times U1)+(B \times U2)$$

wherein A and B are scalar parameters that are functions of the selected angle $\theta$ and the angle $\beta$. Using matrix algebra, this equation may be re-written as follows:

$$\begin{pmatrix} \cos\theta \\ \sin\theta \end{pmatrix} = \begin{bmatrix} 1 & \cos\beta \\ 0 & \sin\beta \end{bmatrix} \begin{pmatrix} \end{pmatrix}$$

Solving this equation for A and B results in the following:

$$A=\sin(\beta-\theta)/\sin \beta;$$

and $B = \sin\theta/\sin\beta$

Recall that S1 and S2 are the voltage signals measured empirically between the respective electrode pairs having the directional vectors of U1 and U2, respectively. Using the voltage measurement S1, the electric fields existing between the first pair of electrodes 302 and 304 may be defined as $E1 = S1/D1,$ wherein D1 is the distance between electrodes 302 and 304. Similarly, the electric field measured between the second pair of electrodes 304 and 306 may be defined as $E2 = S2/D2,$ wherein D2 is the distance between electrodes 304 and 306.

It is known that these two electric fields can be used to approximate the electric field E having the direction vector U between electrode 304 and the selected point 314. The approximation of this electric field may be expressed as follows:

$E = (A \times E1) + (B \times E2),$ where A and B are the scalar parameters discussed above.

Making a series of substitutions, the following is derived for E:

$E = (A \times S1/D1) + (B \times S2/D2)$ $E = ((\sin(\beta-\theta)/\sin\beta) \times (S1/D1)) + ((\sin\theta/\sin\beta) \times (S2/D2))$ Finally, recall that the approximated voltage signal S between the electrode 304 and the point 314 may be described as a function of the electric field E existing between these two points and the electrode spacing D as follows:

$S = D \times E,$ wherein D is the distance between the electrode 304 and point 314.

Thus, S may be expressed as:

$S = D \times [((\sin(\beta-\theta)/\sin\beta) \times (S1/D1)) + ((\sin\theta/\sin\beta) \times (S2/D2))],$ or $S = (D/\sin\beta) \times [(\sin(\beta-\theta) \times (S1/D1)) + (\sin\theta \times S2/D2)]$ Using this description, a close approximation of the amplitude of the signal S may be determined wherein S is the signal that would be measured between electrode 304 and a second electrode positioned at location 314, wherein this selected location 314 is a distance D from electrode 304. In the preferred embodiment, location 314 will be selected such that distance D is fixed at some value between D1 and D2, with D1 and D2 being of relatively the same size. This allows for a better approximation of the signal S when adding the electrical fields associated with the two electrode pairs.

The distance D is a scale factor that does not change the morphology of the time-varying signal S. In that respect, the D can be selected to scale the amplitude of the time-varying signal to the voltage range dictated by circuit requirements. For example, D can be thought of as a programmable amplifier gain that is selected to best allow the signal to be converted by a standard analog-to-digital converter to digital format. In one embodiment, this value is not variable, but is fixed based on circuit requirements and the desired amplitude of the signal S.

The prior description assumes the use of three electrodes for obtaining signals S1 and S2. A four-electrode configuration may also be used for this purpose.

Figure 4:
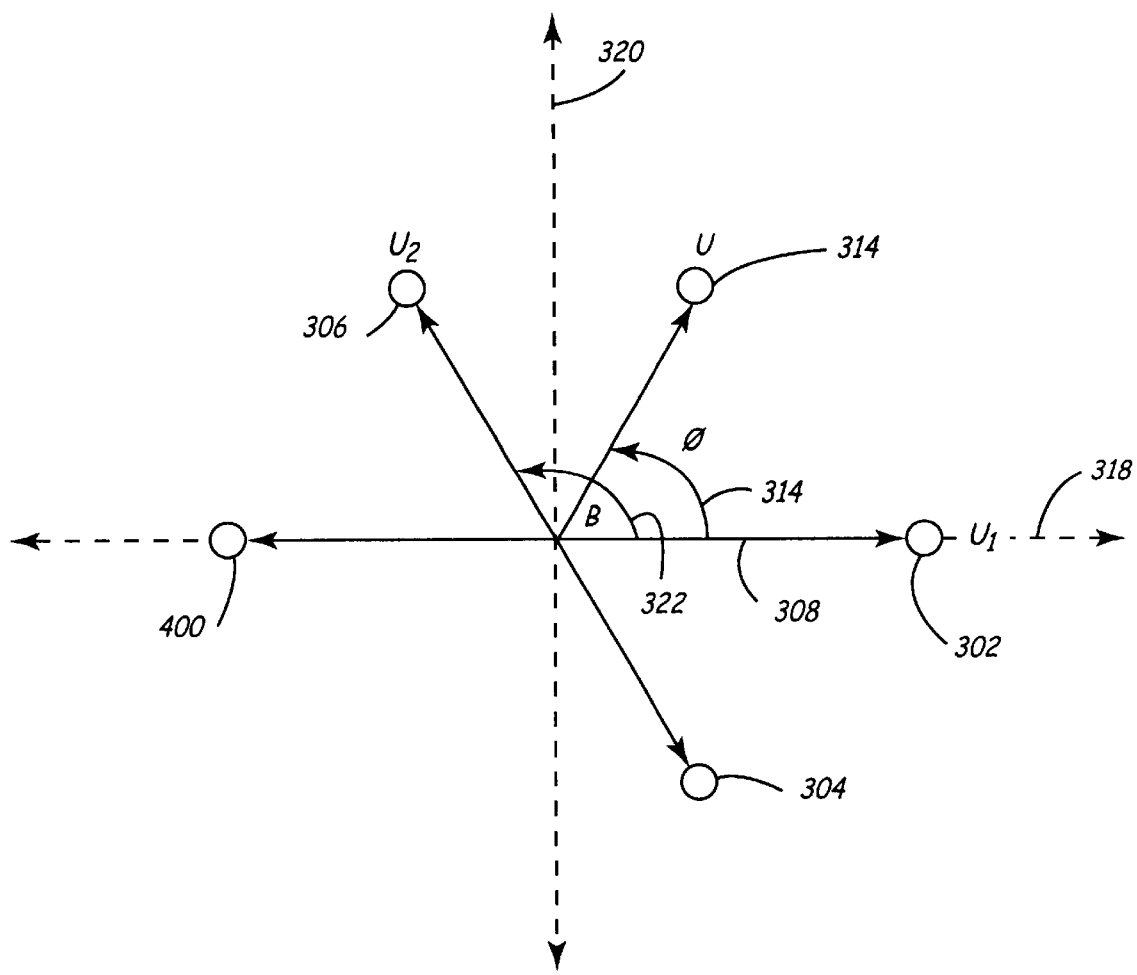
FIG. 4 is a vector diagram illustrating a four-electrode configuration employed within the inventive system.

FIG. 4 is a vector diagram illustrating a four-electrode configuration employed within the inventive system. This diagram includes electrodes 302, 304, and 306 from FIG. 3, and further includes electrode 400. Signal S1 having the directional vector U1 is measured between electrodes 400 and 302, whereas signal S2 having the directional vector U2 is measured between electrodes 304 and 306. The X and Y axes 318 and 320, respectively, are super-imposed such that the point of intersection of these axes coincides with the intersection point of directional vectors U1 and U2. The X axis is positioned to coincide with the directional vector U1 in a manner similar to that discussed above. All other parameters are as discussed above in reference to FIG. 3.

The method set forth in the foregoing paragraphs may be used with this four-electrode configuration to determine the amplitude of signal S, wherein S is a close approximation of the voltage potential that would be measured between electrode 304 and a virtual electrode positioned at location 314.

The above-described method may be performed by a data processing system that receives the measurements S1 and S2 from three or more electrodes. Using the measured values of S1 and S2, the known parameters D1, D2, and $\beta$, and the user-selectable parameters D and $\theta$, the approximate measurement of the signal S may be obtained. A data processing system may perform this analysis in real-time as the values S1 and S2 are measured. Alternatively, previously-stored measurements S1 and S2 may be retrieved from a storage device and processed later according to the above method.

Figure 5:
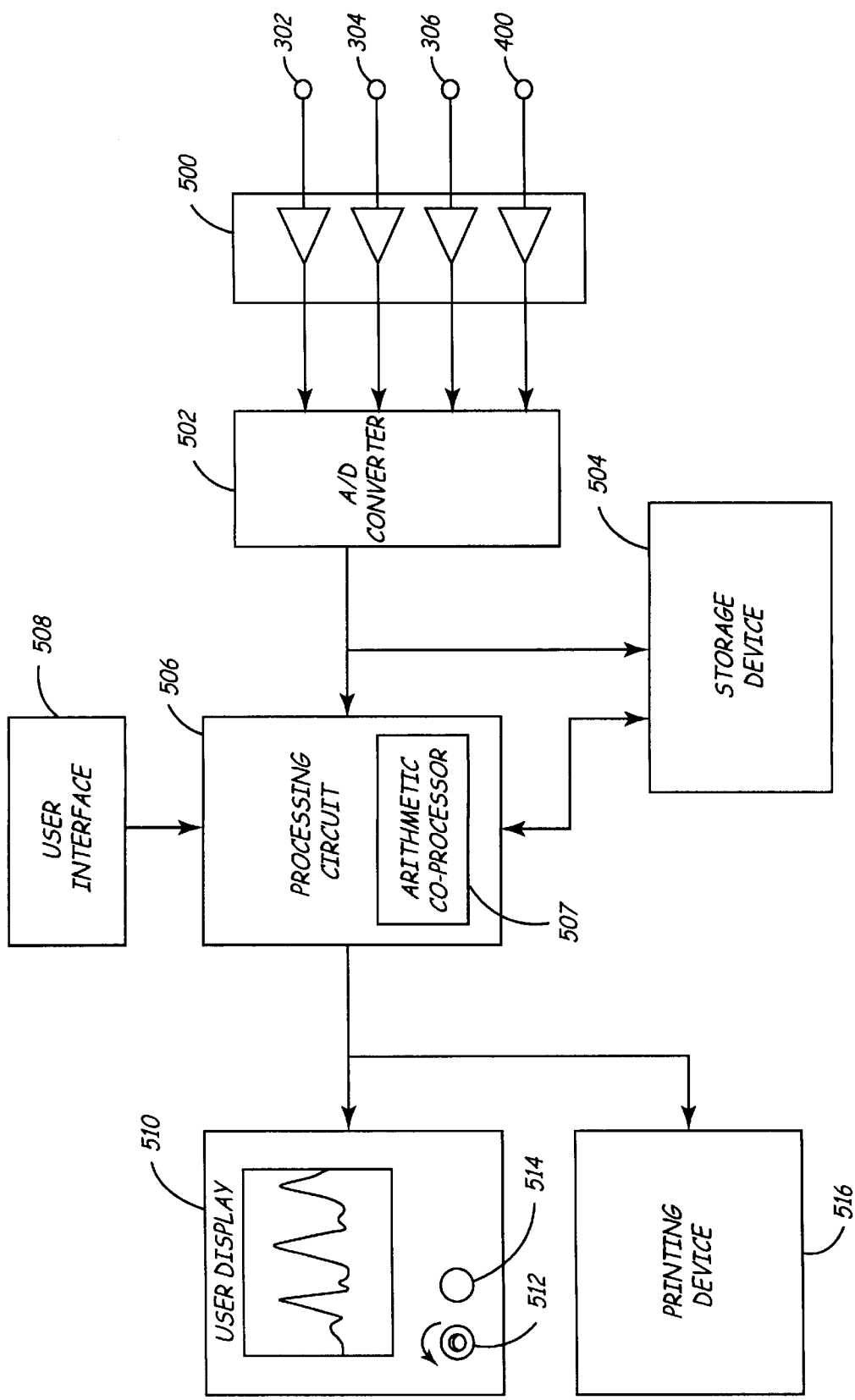
FIG. 5 is a system block diagram of an exemplary system that may perform the above process.

FIG. 5 is a system block diagram of an exemplary system that may perform the above process. Electrodes 302, 304, 306, and 400 are shown, although only three electrodes are required. Electrodes may be positioned on an external surface of a body, or may be a subcutaneous electrode array positioned on the housing of an implantable device. Signals measured by these electrodes are provided to an amplifier device 500, which includes one or more amplifier circuits to amplify, and optionally, filter the signals. The amplified signals are provided to an analog-to-digital (A/D) circuit 502, which converts each of the measured analog signals to a digital representation.

The digitized representative of the measured signals may be stored in storage device 504 for later processing. Storage Device may be, for example, one or more Random Access Memories (RAMs), or another similar type of device. Alternatively, the digitized signals may be provided directly to processing circuit 506 to be processed according to the above-described method so that virtual signal S may be derived. Processing circuit 506 may perform the method under the control of software instructions stored in Storage Device 504, or stored in another memory device. Alternatively, some or all of the inventive method may be performed under hardware control using circuits of the type known to be included in arithmetic co-processors, for example. Such a circuit is shown as co-processor 507 of FIG. 5.

Processing circuit 506 may be coupled to a user interface 508, and may further be coupled to a user display 510. User interface 508 could be, for instance, a keyboard or other control device to allow a user to select desired values for $\theta$ and D so that the signal S may be determined. The signals S1, S2, and/or S may then be displayed on user display 510. If desired, part or all of the user interface may be included on user display 510, such as is shown by exemplary knobs 512 and 514, which may be provided to select $\theta$ and D, for example. Processing circuit 506 may further be coupled to a printing device 516 to generate hard-copy records of the signals.

As discussed above, the current inventive system and method may be performed in conjunction with electrodes that are located within a patient's body. These electrodes may be provided on an external surface of an IMD, for example. This type of subcutaneous electrode array is described in U.S. Pat. No. 5,331,966 referenced above.

When signal measurements are obtained using internally-positioned electrodes, signal measurements S1 and S2 may be temporarily retained in a memory located within an IMD. These signal measurements may be later transferred to an external device such as a programmer or an external monitor for processing and display. Alternatively, signal measurements S1 and S2 could be transferred directly to the external device without first being stored within a storage device of the implanted system. If desired, a portion of the inventive method described above could be completed by a processing circuit included within the IMD. Measured and processed signal data could then be transferred to an external device, so that additional signal processing could be performed, if desired, and the various measured and/or derived signals could be displayed.

Figure 6:
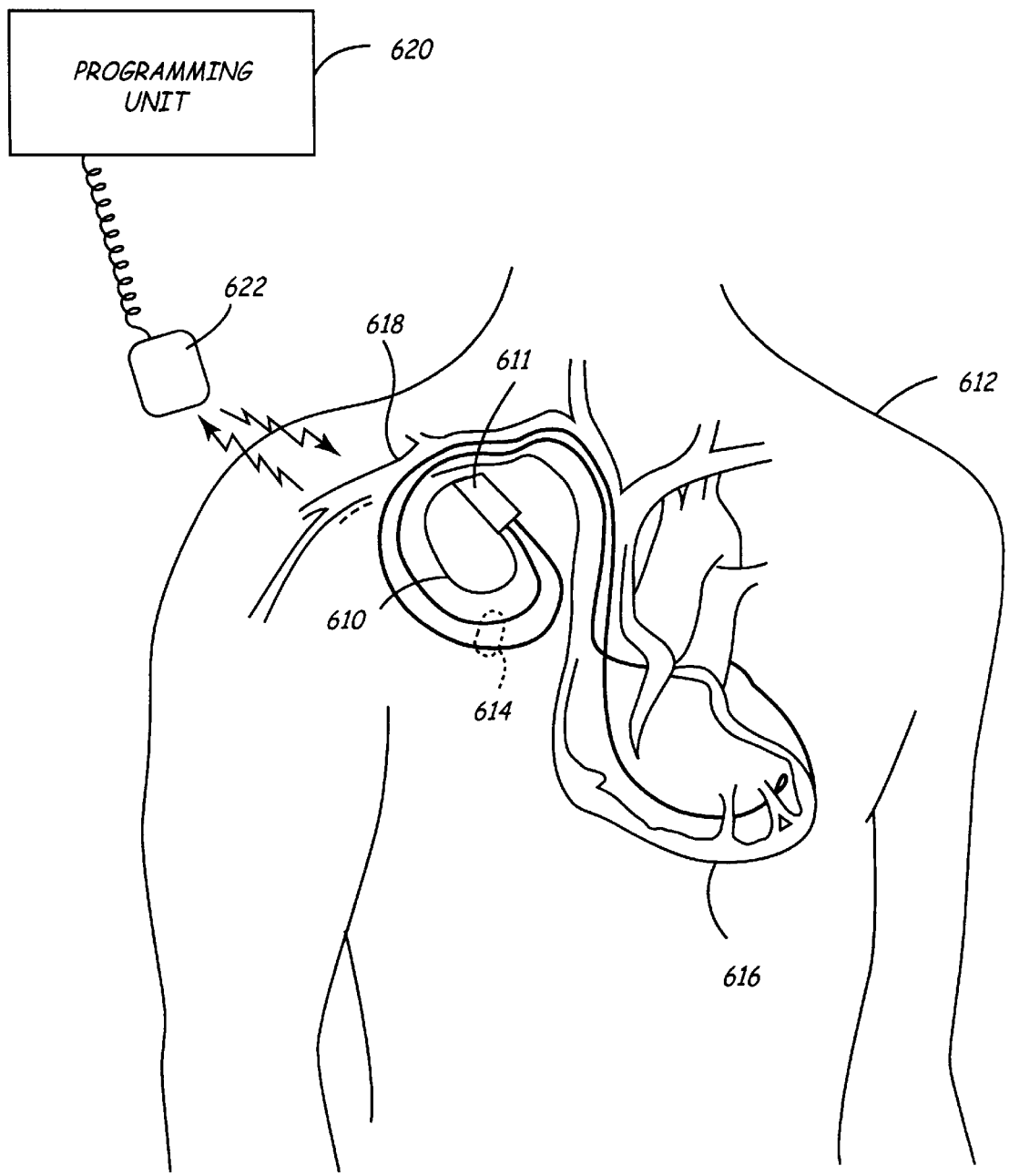
FIG. 6 is an illustration of an Implantable Medical Device (IMD) system adapted for use in accordance with the present invention.

FIG. 6 is an illustration of an Implantable Medical Device (IMD) system adapted for use in accordance with the present invention. The medical device system shown in FIG. 6 includes an implantable device 610, which in this embodiment is a pacemaker implanted in a patient 612. In accordance with conventional practice in the art, pacemaker 610 is housed within a hermetically sealed, biologically inert outer casing, which may itself be conductive so as to serve as an indifferent electrode in the pacemaker's pacing/sensing circuit. One or more pacemaker leads, collectively identified with reference numeral 614 in FIG. 6 are electrically coupled to pacemaker 610 in a conventional manner and extend into the patient's heart 616 via a vein 618. Disposed generally near the distal end of leads 614 are one or more exposed conductive electrodes for receiving electrical cardiac signals and/or for delivering electrical pacing stimuli to heart 616. As will be appreciated by those of ordinary skill in the art, leads 614 may be implanted with its distal end situated in the atrium and/or ventricle of heart 616.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide a communication link between two physically separated components.

Also depicted in FIG. 6 is an external programming unit 620 for non-invasive communication with implanted device 610 via uplink and downlink communication channels, to be hereinafter described in further detail. Associated with programming unit 620 is a programming head 622, in accordance with conventional medical device programming systems, for facilitating two-way communication between implanted device 610 and programmer 620. In many known implantable device systems, a programming head such as that depicted in FIG. 6 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art.

Figure 7:
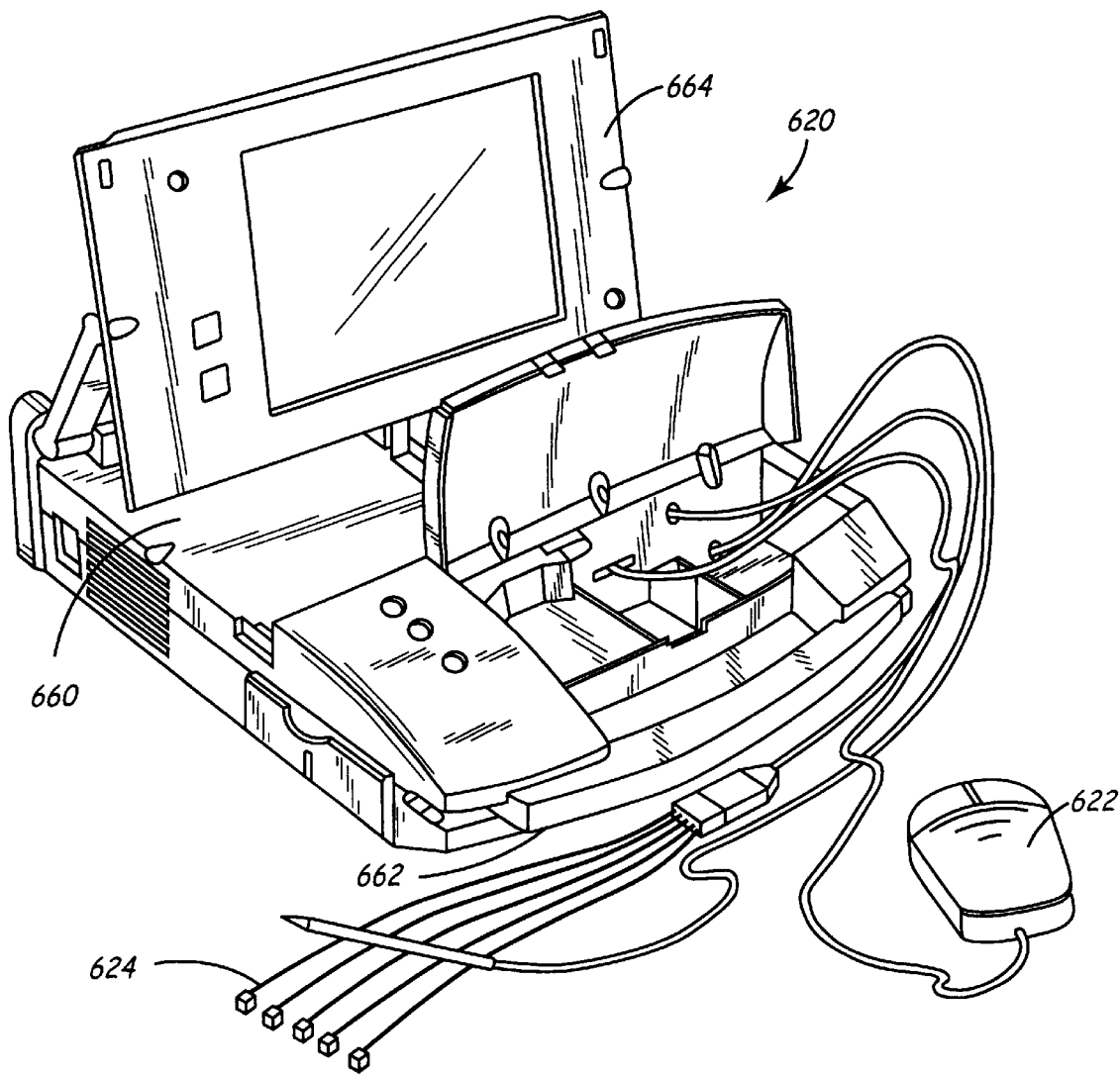
FIG. 7 is a perspective view of programming unit in accordance with the presently disclosed invention.

FIG. 7 is a perspective view of programming unit 620 in accordance with the presently disclosed invention. Internally, programmer 620 includes a processing unit (not shown in FIG. 7) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 7, programmer 620 comprises an outer housing 660, which is preferably made of thermal plastic or another suitably rugged yet relatively lightweight material. A carrying handle, designated generally as 662 in FIG. 7, is integrally formed into the front of housing 660. With handle 662, programmer 620 can be carried like a briefcase. An articulating display screen 664 is disposed on the upper surface of housing 660. Display screen 664 folds down into a closed position (not shown) when programmer 620 is not in use, thereby reducing the size of programmer 620 and protecting the display surface of display 664 during transportation and storage thereof.

A floppy disk drive is disposed within housing 660 and is accessible via a disk insertion slot (not shown). A hard disk drive is also disposed within housing 660, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system. Normally, programmer 620 is equipped with external ECG leads 624. It is these leads that are rendered redundant by the present invention.

In accordance with the present invention, programmer 620 is equipped with an internal printer (not shown) so that a hard copy of a patient's ECG or of graphics displayed on the programmer's display screen 664 can be generated. Several types of printers, such as the AR-100 printer available from General Scanning Co., are known and commercially available.

In the perspective view of FIG. 7, programmer 620 is shown with articulating display screen 664 having been lifted up into one of a plurality of possible open positions such that the display area thereof is visible to a user situated in front of programmer 620. Articulating display screen is preferably of the LCD or electro-luminescent type, characterized by being relatively thin as compared, for example, a cathode ray tube (CRT) or the like.

As would be appreciated by those of ordinary skill in the art, display screen 664 is operatively coupled to the computer circuitry disposed within housing 660 and is adapted to provide a visual display of graphics and/or data under control of the internal computer.

Programmer 620 described herein with reference to FIG. 7 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Programmer 620 could include a user interface for allowing the user to select desired values for $\theta$ and D so that the signal S may be determined. If all data processing is to be performed by a processing circuit internal to an implantable device, these user-selectable values may be transferred from programmer 620 to the implantable device via a communication circuit such as a telemetry circuit (not shown in FIG. 7.)

Figure 8:
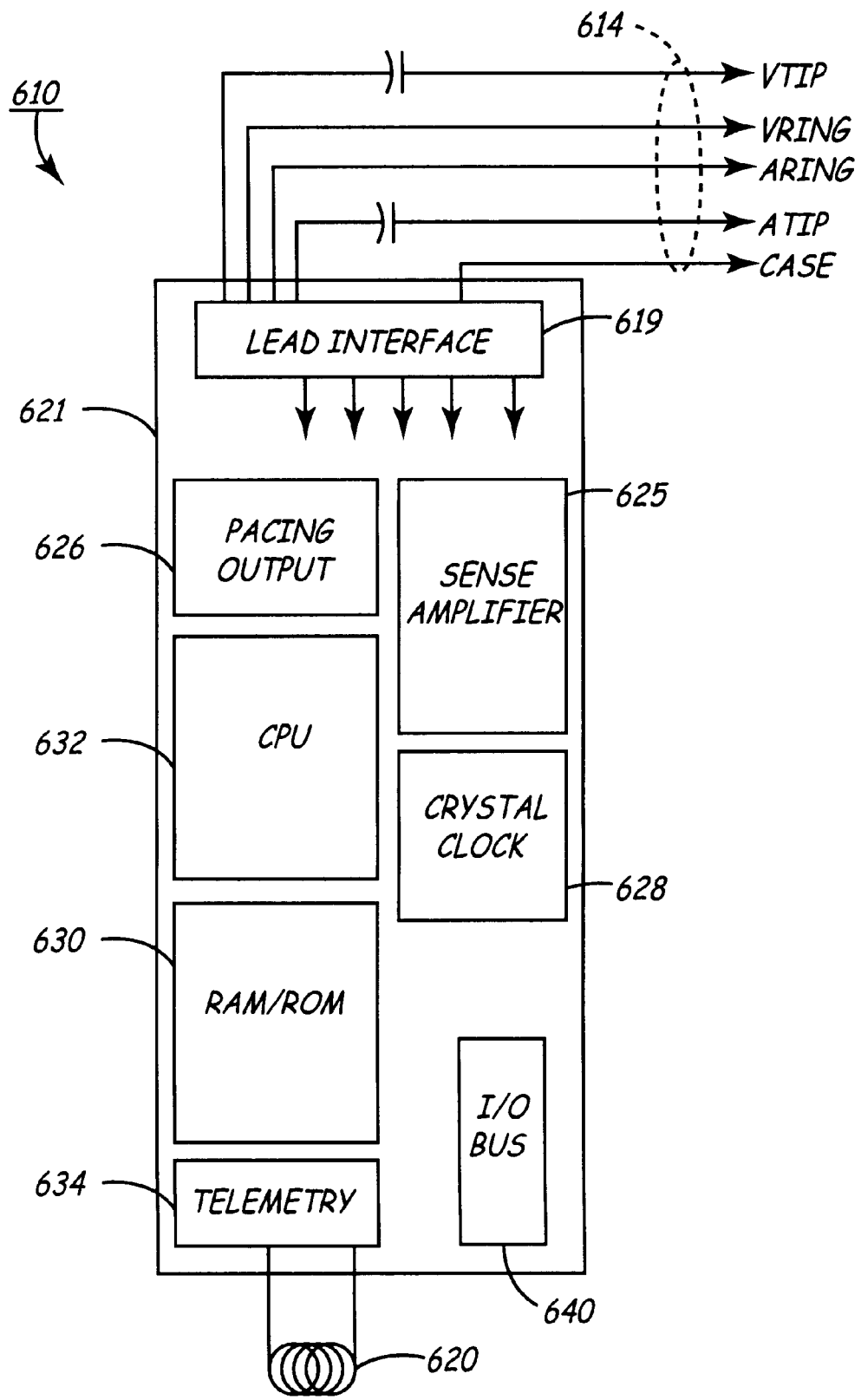
FIG. 8 is a block diagram of the electronic circuitry that makes up the pacemaker in accordance with the presently disclosed invention.

FIG. 8 is a block diagram of the electronic circuitry that comprises pacemaker 610 in accordance with the presently disclosed invention. As can be seen from FIG. 8, pacemaker 610 comprises a primary stimulation control circuit 621 for controlling the device's pacing and sensing functions. The circuitry associated with stimulation control circuit 621 may be of conventional design, in accordance, for example, with what is disclosed U.S. Pat. No. 5,052,388 issued to Sivula et al., "Method and apparatus for implementing activity sensing in a pulse generator." To the extent that certain components of pacemaker 610 are conventional in their design and operation, such components will not be described herein in detail, as it is believed that design and implementation of such components would be a matter of routine to those of ordinary skill in the art. For example, stimulation control circuit 621 in FIG. 8 includes sense amplifier circuitry 625, stimulating pulse output circuitry 626, a crystal clock 628, a random-access memory and read-only memory (RAM/ROM) unit 630, and a central processing unit (CPU) 632, all of which are well-known in the art.

Pacemaker 610 also includes internal communication circuit 634 so that it is capable communicating with external programmer/control unit 620, as described in FIG. 7 in greater detail.

With continued reference to FIG. 8, pacemaker 610 is coupled to one or more leads 614 which, when implanted, extend transvenously between the implant site of pacemaker 610 and the patient's heart 616, as previously noted with reference to FIG. 6. Physically, the connections between leads 614 and the various internal components of pacemaker 610 are facilitated by means of a conventional connector block assembly 611, shown in FIG. 6. Electrically, the coupling of the conductors of leads and internal electrical components of pacemaker 610 may be facilitated by means of a lead interface circuit 619 which functions, in a multiplexer-like manner, to selectively and dynamically establish necessary connections between various conductors in leads 614, including, for example, atrial tip and ring electrode conductors ATIP and ARING and ventricular tip and ring electrode conductors VTIP and VRING, and individual electrical components of pacemaker 610, as would be familiar to those of ordinary skill in the art. For the sake of clarity, the specific connections between leads 614 and the various components of pacemaker 610 are not shown in FIG. 8, although it will be clear to those of ordinary skill in the art that, for example, leads 614 will necessarily be coupled, either directly or indirectly, to sense amplifier circuitry 625 and stimulating pulse output circuit 626, in accordance with common practice, such that cardiac electrical signals may be conveyed to sensing circuitry 625, and such that stimulating pulses may be delivered to cardiac tissue, via leads 614. Also not shown in FIG. 8 is the protection circuitry commonly included in implanted devices to protect, for example, the sensing circuitry of the device from high voltage stimulating pulses.

As previously noted, stimulation control circuit 621 includes central processing unit 632 which may be an off-the-shelf programmable microprocessor or micro controller, but in the present invention is a custom integrated circuit. Although specific connections between CPU 632 and other components of stimulation control circuit 621 are not shown in FIG. 8, it will be apparent to those of ordinary skill in the art that CPU 632 functions to control the timed operation of stimulating pulse output circuit 626 and sense amplifier circuit 625 under control of programming stored in RAM/ROM unit 630. It is believed that those of ordinary skill in the art will be familiar with such an operative arrangement.

With continued reference to FIG. 8, crystal oscillator circuit 628, in the presently preferred embodiment a 32,768-Hz crystal controlled oscillator provides main timing clock signals to stimulation control circuit 621. Again, the lines over which such clocking signals are provided to the various timed components of pacemaker 610 (e.g., microprocessor 632) are omitted from FIG. 8 for the sake of clarity.

It is to be understood that the various components of pacemaker 610 depicted in FIG. 8 are powered by means of a battery (not shown) that is contained within the hermetic enclosure of pacemaker 610, in accordance with common practice in the art. For the sake of clarity in the Figures, the battery and the connections between it and the other components of pacemaker 610 are not shown.

Stimulating pulse output circuit 626, which functions to generate cardiac stimuli under control of signals issued by CPU 632, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 625, which is of conventional design, functions to receive electrical cardiac signals from leads 614 and to process such signals to derive event signals reflecting the occurrence of specific cardiac electrical events, including atrial contractions (P-waves) and ventricular contractions (R-waves). CPU provides these event-indicating signals to CPU 632 for use in controlling the synchronous stimulating operations of pacemaker 610 in accordance with common practice in the art. In addition, these event-indicating signals may be communicated, via uplink transmission, to external programming unit 620 for visual display to a physician or clinician.

Those of ordinary skill in the art will appreciate that pacemaker 610 may include numerous other components and subsystems, for example, activity sensors and associated circuitry. The presence or absence of such additional components in pacemaker 610, however, is not believed to be pertinent to the present invention, which relates primarily to the implementation and operation of communication subsystem 634 in pacemaker 610, and an associated communication subsystem in external unit 620.

Figure 9:
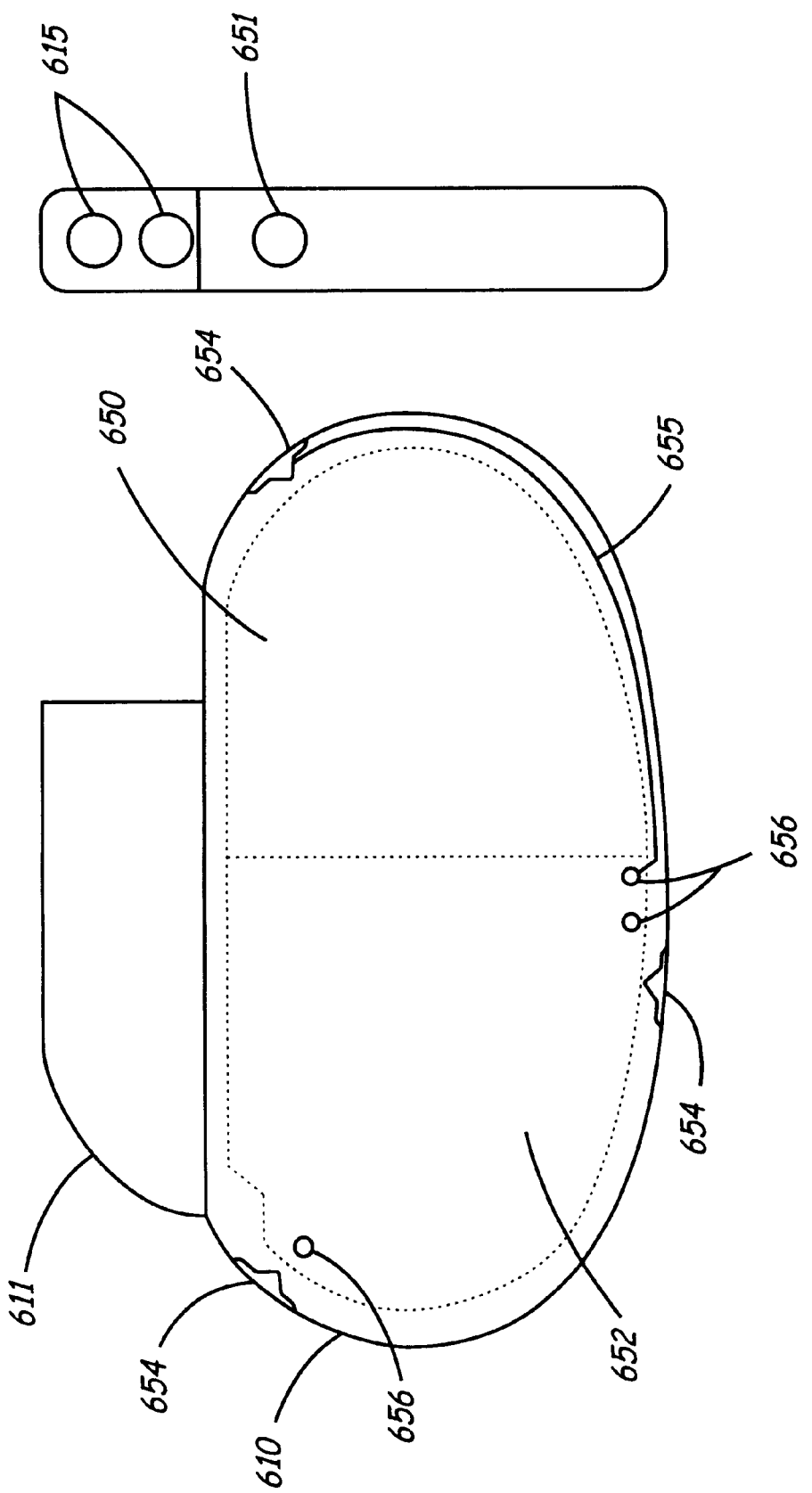
FIG. 9 is a cross sectional view of implanted pacemaker in which the present invention may be practiced.

FIG. 9 is a cross sectional view of implanted pacemaker 610 in which the present invention may be practiced. The major components of pacemaker 610 consist of a hermetic casing in which are housed electronic circuitry 652 and a hermetic power source 650, in this case, a lithium-iodine battery. Lead connector module 611 provides an enclosure into which proximal ends of atrial and ventricular leads may be inserted into openings 615. Lead connector module is connected to pacemaker casing 610 and has electrical connections (not shown) between lead connectors and hermetic feedthroughs (also not shown).

Continuing with FIG. 9, feedthrough/electrode assemblies 651 are welded into place on the flattened periphery of the pacemaker casing. In the embodiment depicted in this figure, the complete periphery of the pacemaker may be manufactured to have a slightly flattened perspective with rounded edges to accommodate the placement of feedthrough/ electrode assemblies such as those practiced in the present invention. These feedthrough/electrode assemblies 654 are welded to pacemaker casing (to preserve hermeticity) and are connected via wire 655 through feedthroughs 656 to electronic circuitry 652.

FIG. 10 is an illustration of the various possible electrode sites that may be located along the perimeter of the implanted pacemaker within the compliant shroud when a subcutaneous electrode array is used to practice the current invention. The spacing between the physical electrodes, as shown, also illustrate the vectors that may be used to detect the cardiac depolarizations. For example, the orthogonal 3-electrode design 672 may use only two potential vectors, as opposed to the equal spacing 3-electrode design 671 that may use all three vectors. The 2-electrode design 671 is not used by the present invention and is presented only as possible in an alternative embodiment. On the other hand, the 4-electrode orthogonal design 673 is one of the preferred embodiments, along with the two 3-electrode designs 671, 672.

Figure 11A:
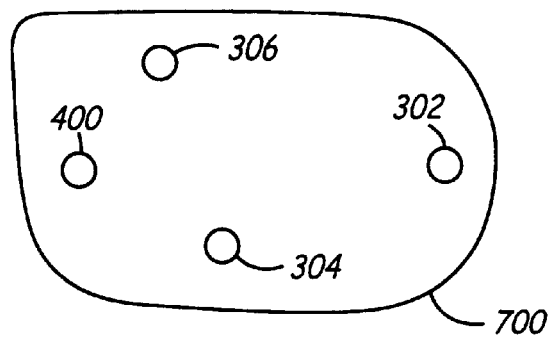
FIG. 11A is a side view of a subcutaneous electrode array including four electrodes provided on the external surface of an Implantable Medical Device.

FIG. 11A is a side view of another embodiment of a subcutaneous electrode array including electrodes 302, 304, 306, and 400 provided on the external surface of IMD 700. As discussed above, as few as three electrodes may be used to practice the current invention.

Figure 11B:
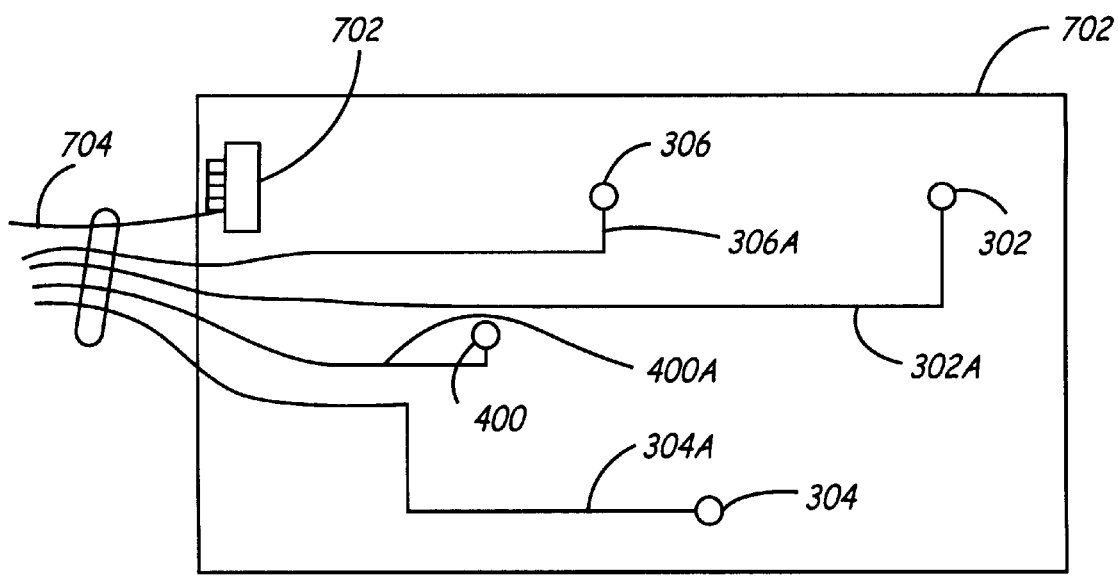
FIG. 11B is a view of an electrode patch of the type that may be applied to an external surface of a body using conductive gel as is known in the art.

FIG. 11B is a view of an electrode patch of the type that may be applied to an external surface of a body using conductive gel as is known in the art. This patch is shown to include four electrodes that may be used in conjunction with the current invention. This illustration shows the electrodes 302, 304, 306, and 400 and associated conductive traces 302A, 304A, 306A, and 400A of the type that may be carried in a cable that is adapted to interconnect to a signal monitoring device that would include a processing circuit such as processing circuit 606. A patch of this type is discussed in the commonly-assigned U.S. patent application having Ser. No. 09/718,689 entitled "System and Method for Non-Invasive Determination of Optimal Orientation of an Implantable Sensing Device" to Lee et al., filed on even date herewith incorporated herein by reference in its entirety.

As discussed in the application to Lee et al., such patches may allow for the re-positioning of the electrodes on the patch. In this instance, the values for $\beta$, D1, and D2 could be set by a user via a bank of switches 702 that are readable via an interface 704 that may be coupled to the processing circuit such as processing circuit 506. This interface allows the processing circuit 506 to obtain the predetermined values utilized to determine signal S in the manner discussed above. It may be noted that if the electrodes are fixed in stationary positions, the values of $\beta$, D1, and D2 may be hardwired on the patch, if desired. In another embodiment, the values may be recorded on the patch to allow a user referencing this patch to easily submit the values to the processing circuit 506 using user interface 508.

Figure 12:
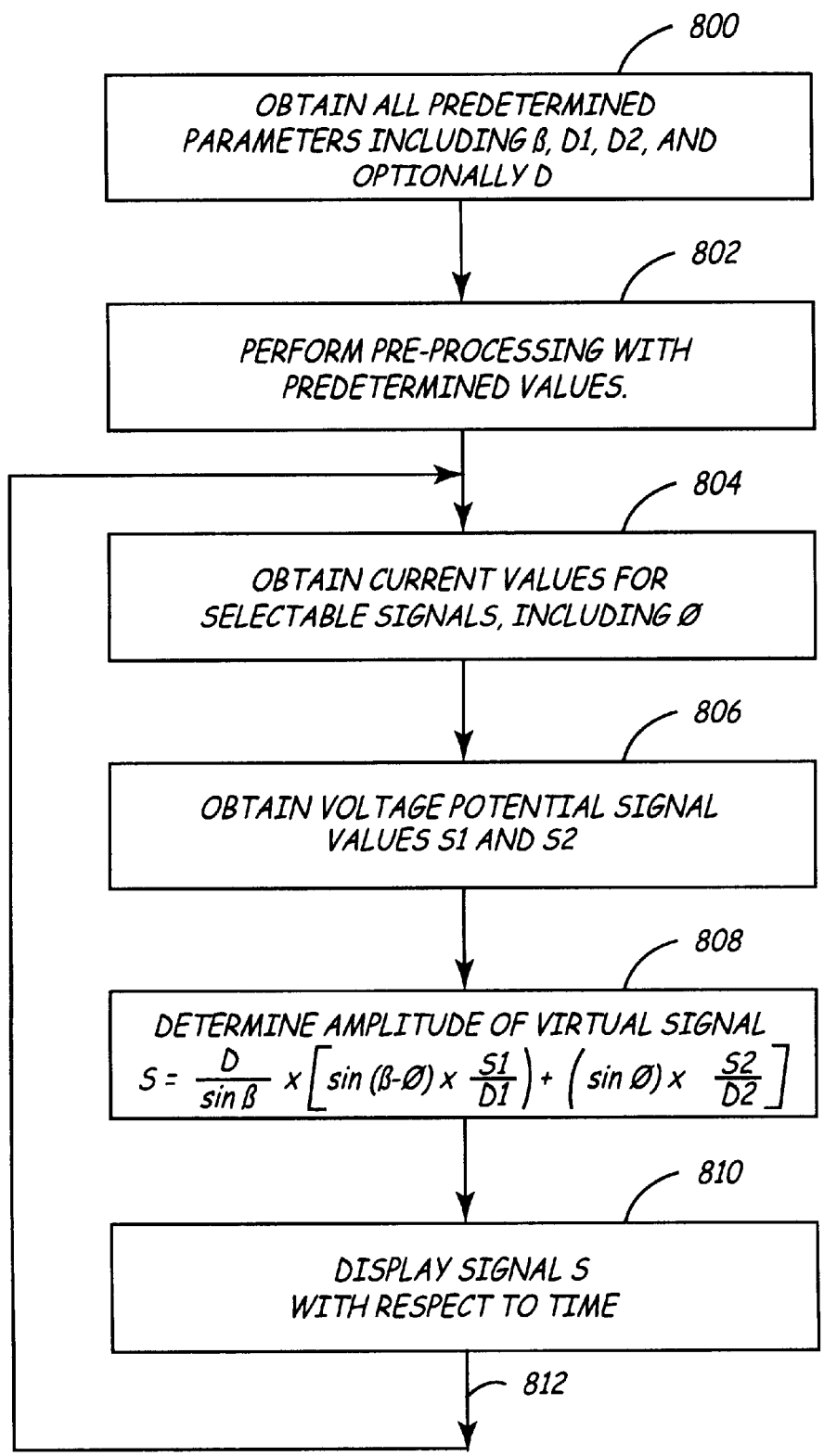
FIG. 12 is a flowchart illustrating the method of the current invention.
Figure 14A:
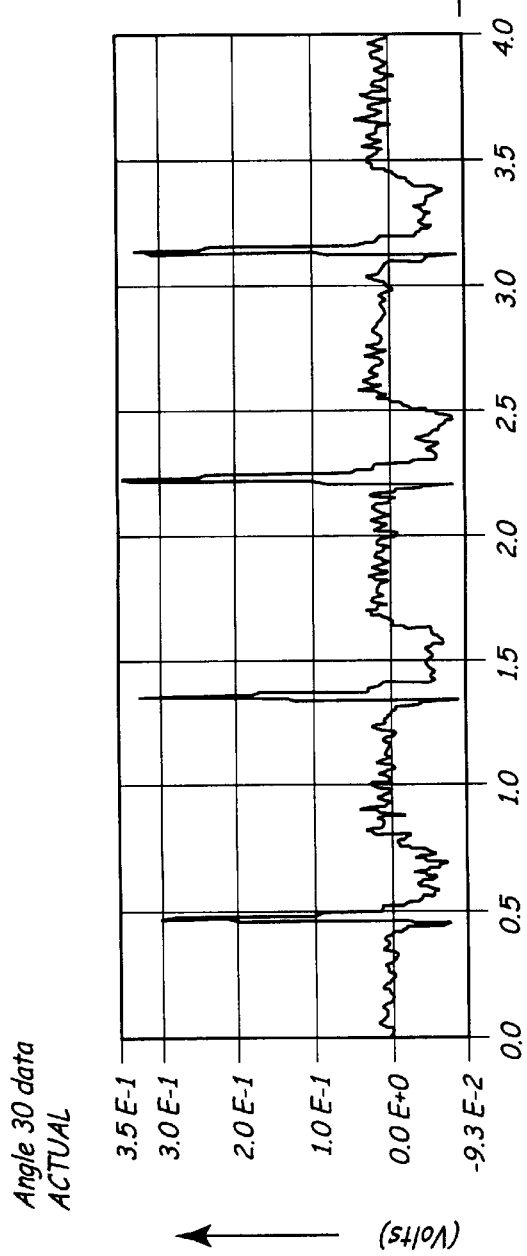
Figure 14B:
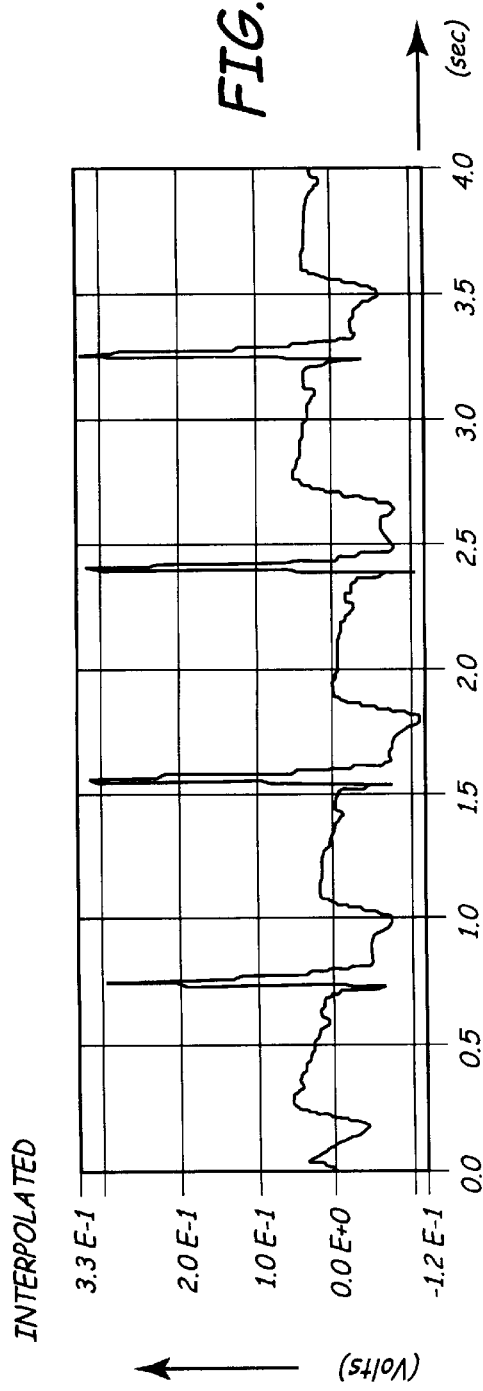
Figure 16A:
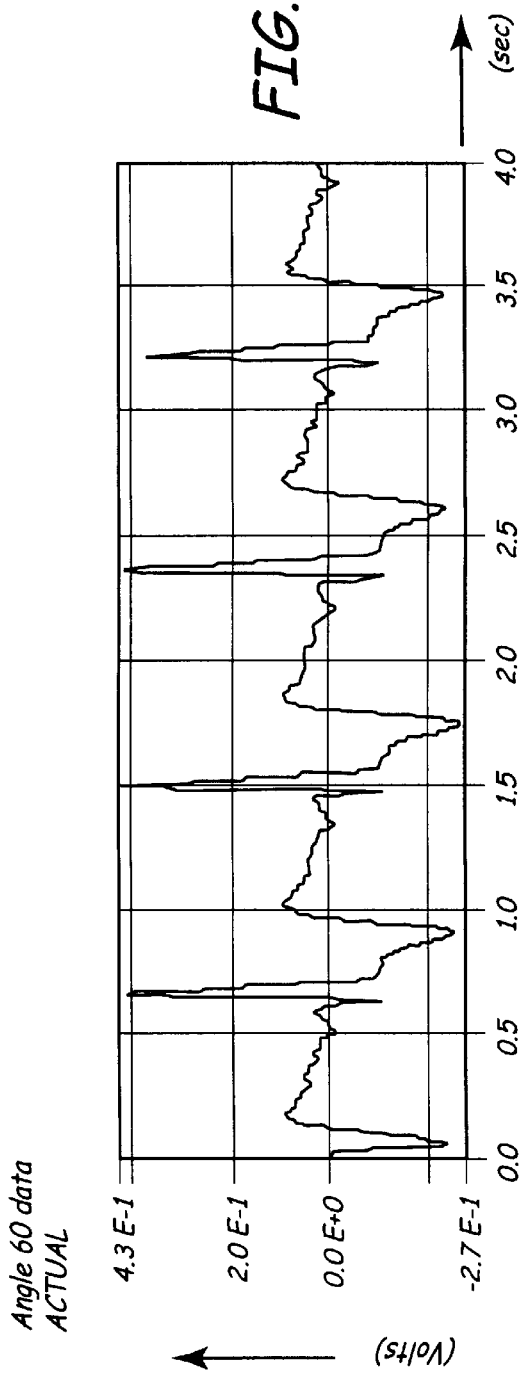
Figure 16B:
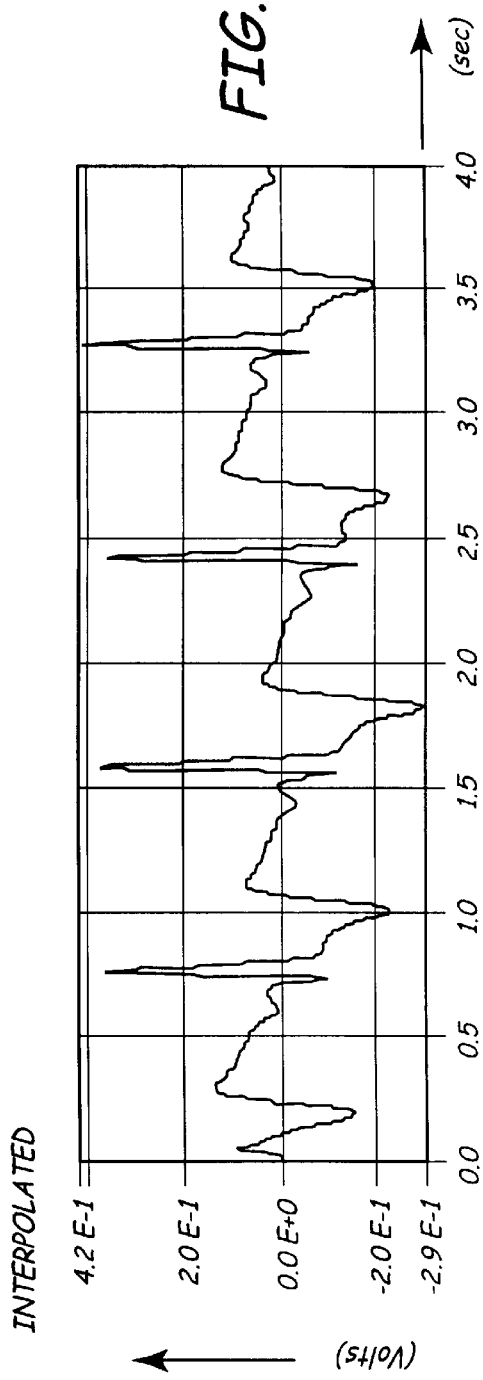
Figure 17A:
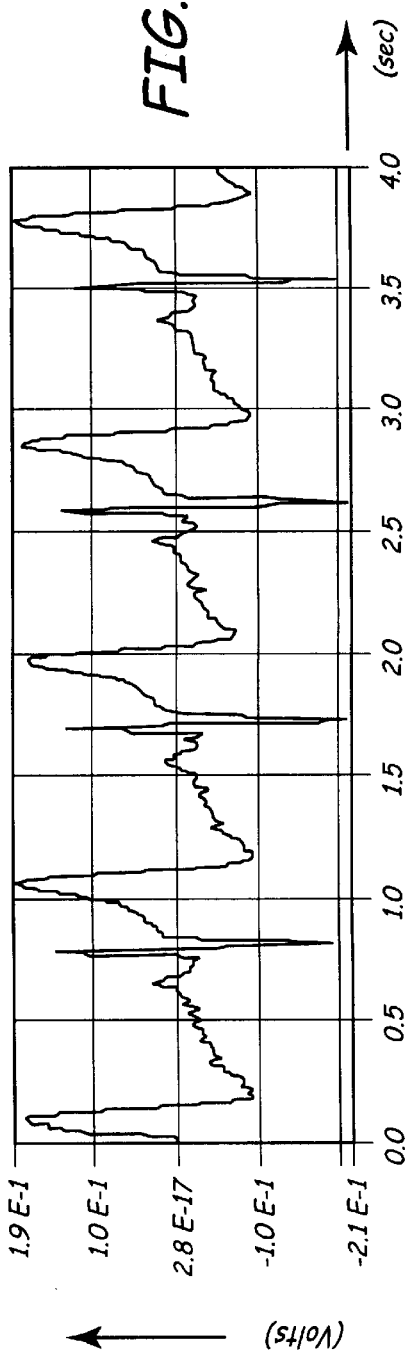
Figure 17B:
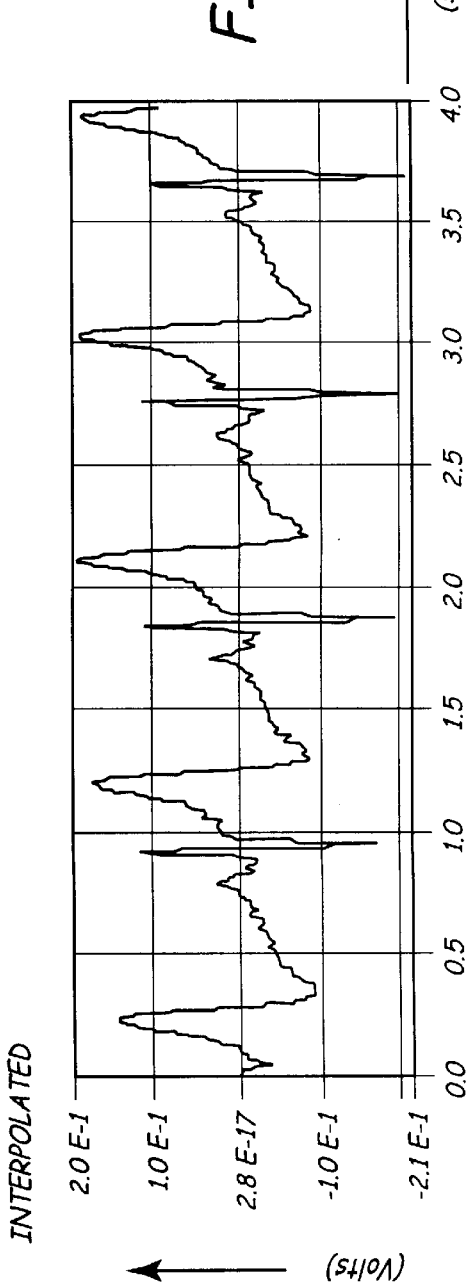
Figure 18A:
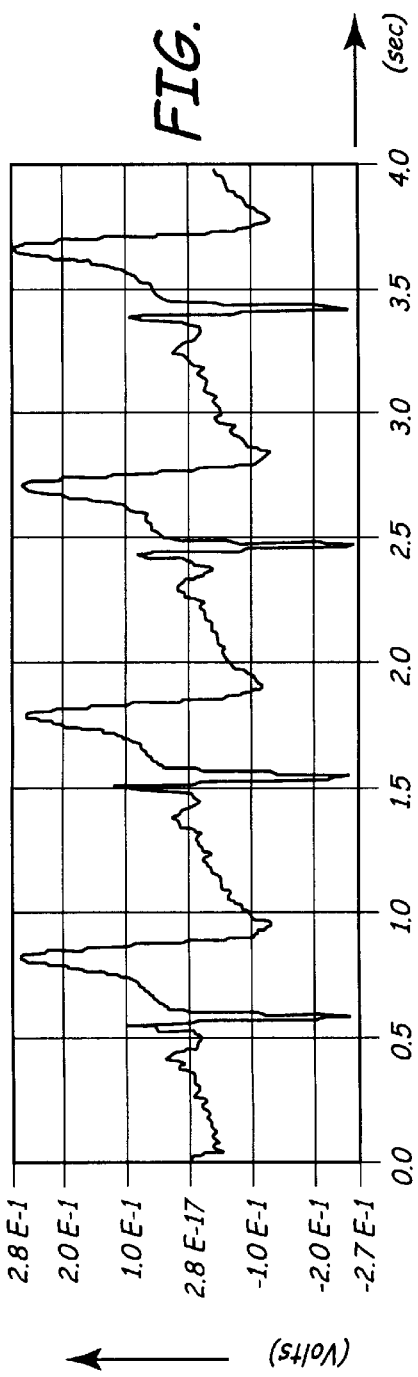
Figure 18B:
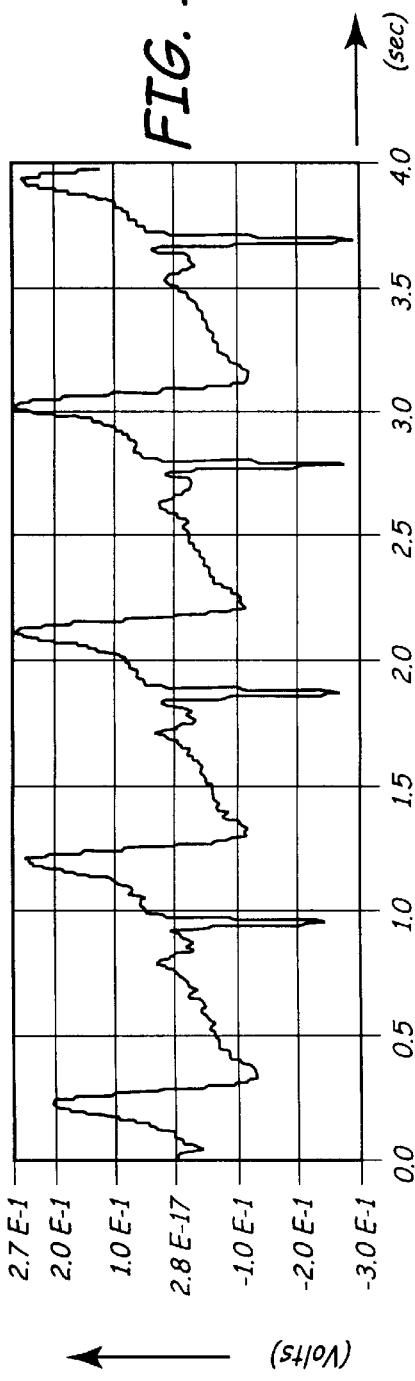
Figure 19A:
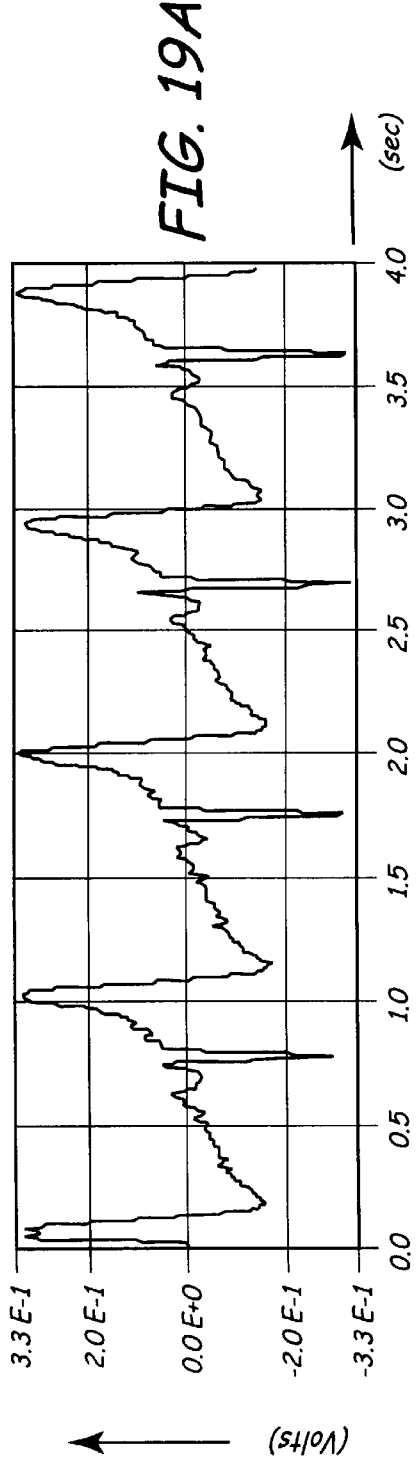
Figure 19B:
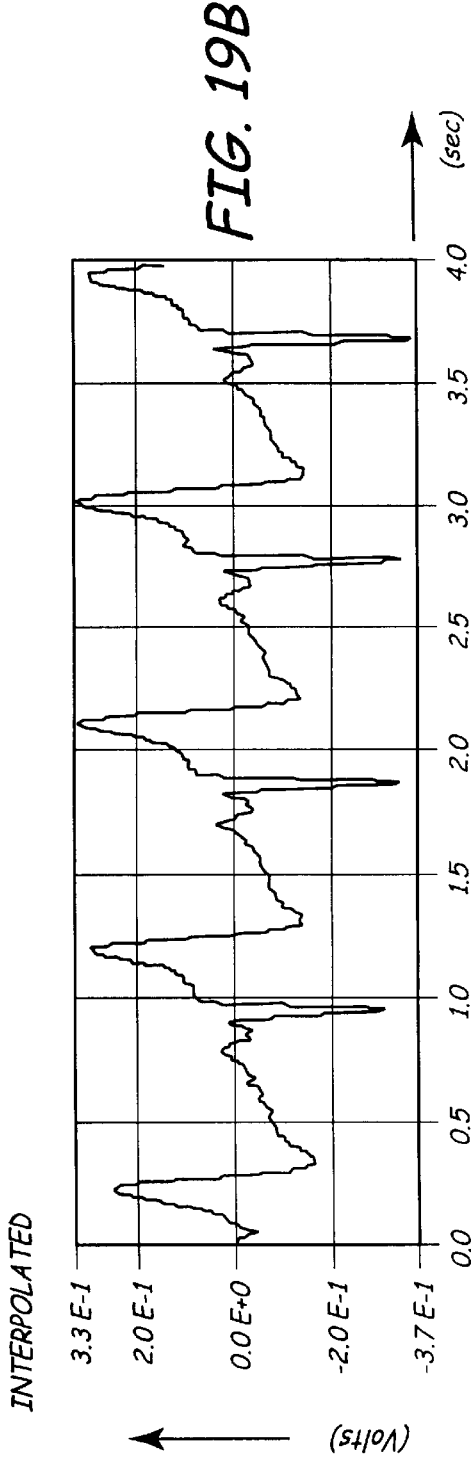

FIG. 12 is a flowchart illustrating the method of the current invention. In step 800, all predetermined parameters are obtained, including $\beta$, D1, D2, and optionally D. These parameters may be entered by a user during initiation of the monitoring session after the user has positioned electrodes on a body. Optionally, these parameters may be readable by a processing circuit such as processing circuit 506 as from jumpers or switches.

If the system is to be utilized with an electrode patch of the type described above, this patch may include jumpers or switches to indicate the values of $\beta$, D1, and D2. The jumper or switch positions may be hard-wired or user-selectable, and may be readable by the processing circuit during step 800. In another embodiment, the values of $\beta$, D1, and D2 need not be readable, but may be listed on the patch to allow the user to easily enter this data during step 800. If the system is always to be used with the same electrode patch, the values for $\beta$, D1, and D2 may be stored in an internal pre-programmed storage device readable by the processing circuit 606. This storage device could be a Read-Only Memory (ROM), or a Random Access Memory (RAM) that is loaded during system initialization. In yet another embodiment wherein the electrodes are part of a subcutaneous electrode array on the surface of an IMD, the values of $\beta$, D1, and D2 may be stored in an internal storage device of the IMD. These values could be obtained from the internal storage device by an internal processing circuit 606, and/or transferred during step 800 to an external programmer 610 for use by processing circuit 606 and/or external programmer 610 in performing the current method. As discussed above, in one embodiment, the value of D is selected to be the larger of D1 and D2. In another embodiment, D may be considered a linear scale factor of the signal S selected based on other circuit limitations or requirements in the system. For example, this value can be selected to generate a signal having a desired amplitude range, and that can readily be processed by the other components of the circuit.

After the predetermined parameters have been obtained, pre-processing may optionally be performed, as shown in step 802. As discussed above, the signal S may be determined by the description:

$$S = (D/\sin \beta) \times [(\sin(\beta-\theta)) \times (S1/D1)) + (\sin \theta \times S2/D2)]$$

Using the known parameters of $\beta$, D1, D2, and optionally D, the values of some portions of this description could be obtained prior to obtaining the user-selectable values, including $\theta$. For example, the values for $(D/\sin \beta)$, S1/D1, and $\sin \theta$ could be obtained to maximize processing efficiency, if desired.

Next, values for the one or more user-selectable parameters may be obtained, including the value of $\theta$, and optionally, the value for D. These may be obtained from user interface 508, for example, or the dials and/or knobs of a user display device 510 as shown in FIG. 5. This is shown in step 804.

In step 806, the measured values of signals S1 and S2 are obtained. These values may be retrieved from a storage device, or may be received directly from a measuring device such as an electrode array on a patch or a subcutaneous electrode array located on the housing of an IMD. In the preferred embodiment, these signals have been filtered and converted to a digital format.

Step 808 involves the determination of the value of S using the description $$S = (D/\sin \beta) \times [(\sin(\beta-\theta)) \times (S1/D1)) + (\sin \theta \times S2/D2)].$$

In step 810, this signal may be displayed as a function of time, and the process may be repeated, as indicated by arrow 812.

It will be appreciated that the above-described method includes steps that could be performed in sequences other than as shown in FIG. 8, and the ordering of steps is therefore to be considered exemplary in nature, and not limiting.

As discussed above, the inventive system and method provides an efficient means of improving the morphology of a waveform according to the aspect of interest. For example, in certain instances, the T wave becomes the most important aspect of an ECG signal. Using the current invention, $\theta$ may be adjusted until a virtual signal S is located that most optimally emphasizes this portion of the cardiac signal. Other selections for θ may be made that result in an enlarged P, or QRS waveforms. Conversely, a minimum QRS waveform may be desired so that P-waves are easier to detect. The angle θ may be selected to obtain a desired polarity for a particular portion of a waveform. For example, θ may be selected so the QRS complex of an ECG signal is positive or negative-going, depending on user preference.

According to another application of the inventive system and method, a value of θ may be selected that modifies the width of a particular waveform segment. For example, it may be desirable to locate a value for θ that provides the widest QRS complex. This view will therefore emphasize changes in the width of the QRS complex. This can be useful, for example, when analyzing the V—V timing in a biventricular pacing device wherein the goal is to adjust the pacing delay to obtain the most narrow QRS complex. This can also be useful in diagnosing heart failure patients, since QRS width changes are used to indicate changing patient conditions. In yet another instance, the width of the QRS complex is used to distinguish between Ventricular Tachyarrhythmias (VTs) and Supra Ventricular Tachyarrhythmias (SVTs). Similarly, θ may be selected to locate a view providing the longest QT interval, since this view will emphasize changes in the QT interval. This allows a clinician to more readily detect QT dispersions that occur in people that are at risk for sudden death.

In one embodiment, the angle θ may be selected by rotating a knob through 360 degrees, with each position of the knob corresponding to a respective selection for the angle θ. In another embodiment, θ is selectable in predetermined increments. For example, θ may be selectable in increments of 15 degrees.

As discussed above, the virtual signal S closely approximates the signal that would be measured by electrodes positioned to have the angle θ and the distance D as shown in FIG. 3.

FIG. 13A is a graph of a measurement physiological voltage signal with respect to time wherein the signal is measured using an electrode pair positioned to have an angle θ of 15 degrees with respect to a first measured signal in the manner shown in FIG. 3.

FIG. 13B illustrates the comparable virtual signal S which approximates the measured signal shown in FIG. 13A. This signal S is determined using the measured signal values S1 and S2 according to the inventive method discussed above. It may be noted that the graphs of FIGS. 13A and 13B appear shifted in time with respect to each other. For example, the measured waveform peak occurring at a time of approximately 0.5 seconds in FIG. 13A corresponds to the approximate peak value occurring at around 0.75 seconds in FIG. 13B. This time offset is merely an artifact of the data collection procedure. If the graphs are adjusted to remove this arbitrary shift in time, the waveform morphology as shown in FIG. 13B can be seen to closely approximate the measured waveform of FIG. 13A.

Figure 20A:
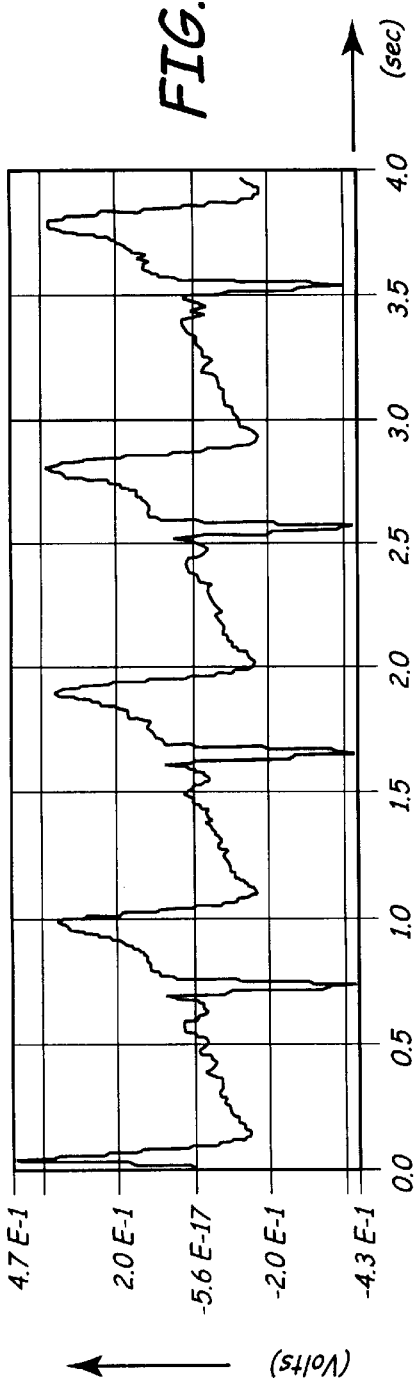
Figure 20B:
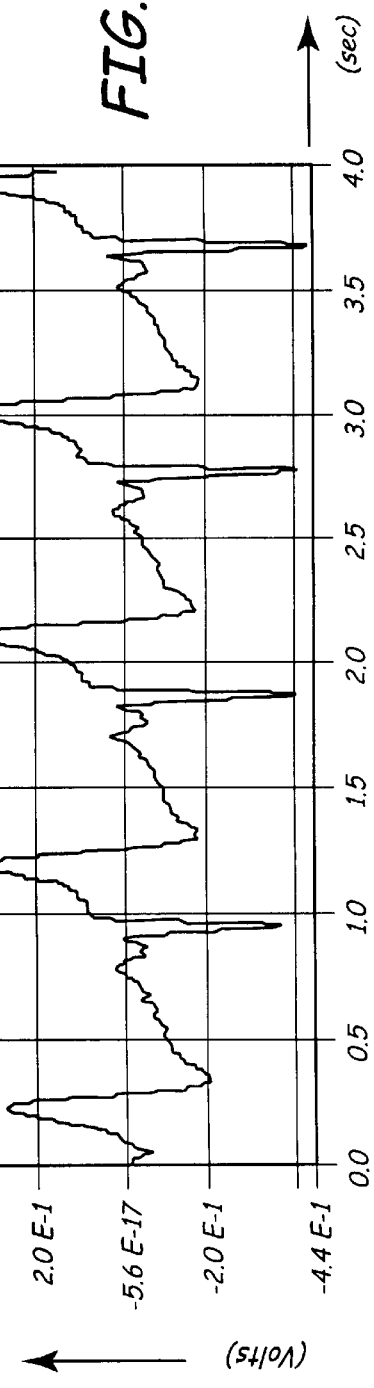

In a similar manner as discussed above in reference to FIGS. 13A and 13B, FIGS. 14A through 20B are graphs comparing measured physiologic signal values to respective interpolated values for various values of angle θ. These Figures illustrate the manner in which a variation in the angle θ changes the waveform morphology. For example, FIG. 13B shows the signal value S for an ECG signal that is derived using an angle θ of 15 degrees. The QRS complex in this Figure has a relatively large positive amplitude. In contrast, the derived waveform shown in FIG. 20B for an angle θ of −60 degrees shows the QRS complex as having an amplitude that is slightly less than 0 volts. However, the signal at this angle emphasizes the T-waves, such as the T-wave occurring at approximately 1.25 seconds. Therefore, a clinician interested in viewing a positive-going QRS complex could select the waveform S at an angle θ of 15 degrees, whereas another clinician might select the signal S at an angle θ of −60 if the T-waveforms are of particular interest.

As noted above, the current inventive system and method may be utilized to derive measurements for an infinite number of virtual electrode positions located within the plane of the measured signals. For example, in one embodiment, processing circuit 560 or 660 may be used to generate the time-varying waveform for S throughout a range of values for θ. Each waveform S could then be evaluated for a predetermined criterion. For example, the set of criterion for an ECG waveform could specify that the waveform S of interest is that waveform having the most positive-going QRS complex. Using this criterion, the value for θ that provides such a waveform could then be selected to display S for all future measures of S1 and S2.

Figure 21:
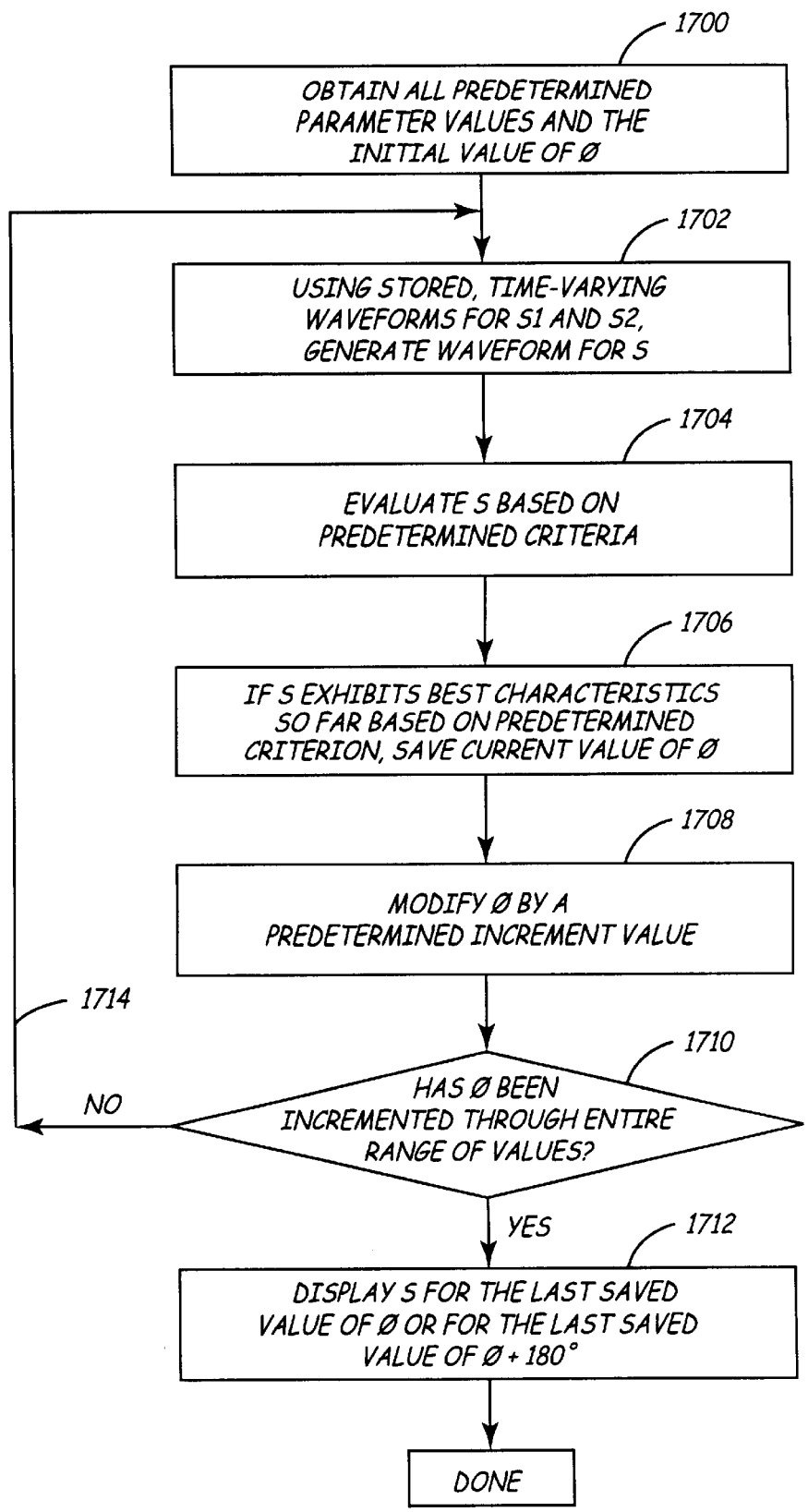
FIG. 21 is a flowchart illustrating the derivation of the waveform S using stored values of S1 and S2 throughout a range of values for the angle θ.

FIG. 21 is a flowchart illustrating the derivation of the waveform S using stored values of S1 and S2 throughout a range of values for the angle θ. This allows an optimal waveform morphology to be selected for a desired purpose. In step 1700, parameters values are obtained for all predetermined values including D1, D2, and the angle β. Additionally, and initial value for the angle θ is obtained. In step 1702, the time-varying signal for S is determined using the current value of the angle θ and stored values for S1 and S2. This waveform is then evaluated against a predetermined set of criterion, as illustrated in step 1704. For example, this criterion may indicate that the waveform S exhibiting the most positive-going QRS complexes should be selected for display. If the current derived waveform S exhibits the desired criterion better than any previously derived waveform S, the current value for angle θ is retained, as illustrated in step 1706. Then the value for θ is modified by a predetermined incremental value, as shown in step 1708. For example, the angle θ may be incremented or decremented by 0.5 degrees. If the value for θ has then been modified throughout an entire predetermined range of desired values such as the range 0–360 degrees, the waveform for S may then be displayed for the retained value of θ, since this is the value of θ that best produces the desired waveform morphology. This value of θ may then be used to display future signals in real time using the current electrode positions, if desired. This is as shown in decision step 1710 and step 1712, respectively. If the entire range of values for θ has not yet been tested, steps 1702 through 1710 are repeated, as shown by arrow 1714.

In one embodiment, processing could be optimized by generating various waveforms for an angle θ that varies between 0 and 180 degrees. The polarity of a selected waveform could then be reversed if this range of angles did not result in the selected portion of the waveform having a desired polarity. For example, assume that a set of generated waveforms is calculated for an angle θ varied between 0 and 180 degrees in predetermined increments. Further assume this results in one of the waveforms derived for an angle $θ_1$ having a maximum negative value for the QRS waveform complex. If the selectable criterion dictates the most positive-going QRS waveform is to be selected, it may be deduced that the selected waveform is that derived at an angle ($θ_1$+180). This waveform may be derived using the above-described method, or may alternatively be derived by inverting all signal values associated with the waveform S generated for the angle $\theta_1$.

It is to be understood that even though numerous embodiments and advantages of the present invention have been set forth in the foregoing description, the above disclosure is illustrative only, and changes may be made in detail yet remain within the broad principles of the invention. For example, although the above examples discuss the use of ECG signals with the current invention, it may be understood other physiologic voltage signals occurring in a body may be employed with the inventive system and method. Therefore, the present invention is to be limited only by the appended claims.

What is claimed is:

1. A system for having at least three electrode for measuring voltage signals S1 and S2 between a first and second pair of the at least three electrodes, respectively, and wherein one of the at least three electrodes is a common electrode used in both said first and second pairs, the system for automatically deriving an approximation of a voltage signal S existing between the common electrode and a selected point, the system comprising:
   a user interface to allow a user to select a value for an angle $\theta$, wherein the angle $\theta$ is the angle measured between a directional vector associated with a predetermined one of the first and second pair of the at least three electrodes and a directional vector U associated with the voltage signal S; and
   a processing circuit coupled to the user interface to derive the amplitude of the voltage signal S as a function of S1, S2, $\theta$, an angle $\beta$ between the first and second pairs.

2. The system of claim 1, wherein the processing circuit further includes means to derive the amplitude of the voltage signal S as a function of distances D1 and D2 existing between electrodes of the first and second pairs of the at least three electrodes, respectively.

3. The system of claim 2, and further including a user display coupled to the processing circuit to display the voltage signal S varied over time.

4. The system of claim 2, and further including a memory coupled to processing circuit to store predetermined values for S1, S2, and $\beta$.

5. The system of claim 2, wherein the processing circuit further includes means for deriving the amplitude of the voltage signal S as a function of a distance D between the common electrode and the selected point.

6. The system of claim 5, wherein the user interface includes a device to allow the user to select a value for the distance D.

7. The system of claim 2, wherein the processing circuit includes means to derive a voltage waveform for the voltage signal S as a function of time from voltage signals S1 and S2 measured over time.

8. The system of claim 7, wherein the memory includes circuits to store one or more predetermined waveform criterion, and wherein the processing circuit includes means to derive the voltage waveform for the voltage signal S as a function of time for an angle $\theta$ varied at a predetermined increment between a predetermined range of angles, and for selecting an optimal one of the derived voltage waveforms for display to the user based on the one or more predetermined waveform criterion.

9. The system of claim 8, wherein the predetermined range of angles is between 0 and 360 degrees.

10. The system of claim 8, wherein the processing circuit includes means to invert the polarity of the optimal one of the derived voltage waveforms prior to displaying it to the user.

11. A system for generating a derived signal S indicative of a time-varying voltage signal that would be measured between electrodes positioned at first and second points within a body, the system comprising:
   at least three electrodes to provide a first predetermined electrode pair and a second predetermined electrode pair, the first predetermined electrode pair to measure a time-varying signal S1 having a directional vector U1, and the second predetermined electrode pair to measure a time-varying signal S2 having a directional vector U2; and
   a processing circuit coupled to receive the time-varying voltage signals S1 and S2, and to derive the signal S along a directional vector U that is an approximation of a signal that would be measured between the first point defined by the intersection of directional vectors U1 and U2, and the second point, the signal S being derived as a function of an angle $\theta$ that is the angle measured between the directional vector U1 and the directional vector U.

12. The system of claim 11, and further including a user display coupled to the processing circuit to display the time-varying voltage signal S.

13. The system of claim 11, wherein the processing circuit including circuits to derive the signal S as a further function of an angle $\beta$ that is the angle measured in a predetermined direction between the directional vector U1 and the directional vector U2.

14. The system of claim 13, wherein the processing circuit further including circuits to derive the signal S as a further function of a distance D between the selected point and the common electrode.

15. The system of claim 14, wherein the processing circuit further including circuits to derive the signal S as a further function of a distance D1 between the first and the common electrodes, and a distance D2 between the second and the common electrodes.

16. The system of claim 11, wherein at least a first portion of the processing circuit is located within an implantable medical device.

17. The system of claim 16, wherein the at least three electrodes are located on an external surface of the implantable medical device to provide time-varying voltage signals S1 and S2 to the first portion of the processing circuit.

18. The system of claim 17, wherein the processing circuit includes a second portion external to the body, the system includes a communication circuit within the implantable medical device and coupled to the first portion of the processing circuit, the communication circuit to transfer the time-varying voltage signals S1 and S2 to the second portion of the processing circuit.

19. The system of claim 18, wherein derivation of the time-varying voltage signal S requires several steps, and wherein the first portion of the processing circuit includes means to perform one or more of the several steps, and whereby a partially-derived signal is transferred by the communication circuit to the second portion of the processing circuit to complete the one or more of the several steps.

20. The system of claim 18, wherein derivation of the time-varying voltage signal S requires several steps, and wherein the first portion of the processing circuit includes means to perform all of the several steps, and whereby the time-varying voltage signal S is transferred by the communication circuit to the second portion of the processing circuit.

21. The system of claim 18, wherein derivation of the time-varying voltage signal S requires several steps, and wherein the second portion of the processing circuit includes means to perform all of the several steps.

22. The system of claim 11, wherein the processing circuit includes means to automatically vary the angle θ at predetermined increments over a predetermined voltage range to determine an optimal time-varying voltage signal S.

23. The system of claim 22, wherein the processing circuit includes means to determine an optimal time-varying voltage signal S as a function of at least one predetermined waveform criterion.

24. The system of claim 11, wherein the common, first, and second electrodes are located on an electrode patch adapted for application to an external surface of the body.

25. The system of claim 24, wherein the electrode patch includes a readable device to determined the values of D1, D2, and β.

26. A method executed by a processing circuit for approximating a physiologic voltage signal S between two points within a body spaced a distance D apart from one another, the method comprising the methods of:
   a.) measuring two signals S1 and S2 having directional vectors U1 and U2, respectively;
   b.) determining an angle θ measured between the directional vector U1 and a directional vector U of the voltage signal S; and
   c.) approximating the physiologic voltage signal S as a function of the angle θ.

27. The method of claim 26, and further including the method of d.) displaying the physiologic voltage signal S on a user display.

28. The method of claim 27, wherein step b.) is performed by obtaining the angle θ as a selection from a user.

29. The method of claim 27, wherein the processing circuit includes at least a first and second processing portion, the first processing portion being located inside the body and the second processing portion being located outside the body, wherein the first processing circuit further includes a communication circuit, wherein step c.) includes multiple processing steps, and further including the methods of:
   c1.) performing one or more of the multiple processing steps to obtain intermediate processing results;
   c2.) transferring the intermediate processing results to the second processing portion via the communication circuit; and
   c3.) executing remaining ones of the multiple processing steps by the second portion to obtain the physiologic voltage signal S.

30. The method of claim 27, wherein the processing circuit includes at least a first and second processing portion, the first processing portion being located inside the body and the second processing portion being located outside the body, wherein the first processing circuit further includes a communication circuit, wherein step c.) further including the methods of:
   c1.) transferring signals S1 and S2 to the second processing portion via the communication circuit; and
   c2.) approximating, by the second processing portion, the physiologic voltage signal S as a function of the angle θ.

31. The method of claim 27, wherein the processing circuit includes at least a first and second processing portion, the first processing portion being located inside the body and the second processing portion being located outside the body, wherein the first processing circuit further includes a communication circuit, wherein step c.) further including the methods of:
   c1.) approximating, by the first processing portion, the physiologic voltage signal S as a function of the angle θ; and
   c2.) transferring signals S1 and S2 to the second processing portion via the communication circuit.

32. The method of claim 26, and further including the steps of
   d.) repeating steps a.) through c.) for all values of the angle θ existing at predetermined increments within a predetermined range of angles to generate respective physiologic voltage signals, and
   e.) selecting an optimal physiologic voltage signal from among all of the respective physiologic voltage signals based on predetermined criterion.

33. The method of claim 32, wherein step e.) is performed using criterion describing waveform morphology of an ECG signal.

34. The method of claim 32, wherein step a.) includes selecting directional vectors U1 and U2, and wherein the function of step c.) is further a function of β, a selectable angle between directional vectors U1 and U2.

35. The method of claim 26, wherein step c.) includes the step of approximating the physiologic voltage signal S as a function of a selectable value provided for the distance D.

* * * * *